(12) United States Patent
Hanajima et al.

(10) Patent No.: US 10,741,282 B2
(45) Date of Patent: Aug. 11, 2020

(54) MEDICAL TOOL WORK SUPPORT SYSTEM, MEDICAL TOOL WORK SUPPORT METHOD, AND MEDICAL TOOL WORK SUPPORT PROGRAM

(71) Applicants: Roland DG Corporation, Hamamatsu-shi, Shizuoka (JP); National University Corporation Hamamatsu University School of Medicine, Hamamatsu-shi, Shizuoka (JP)

(72) Inventors: Masaki Hanajima, Hamamatsu (JP); Takeshi Tsuji, Hamamatsu (JP); Takaaki Kokubo, Hamamatsu (JP); Naomi Ishino, Hamamatsu (JP)

(73) Assignees: ROLAND DG CORPORATION, Shizuoka (JP); NATIONAL UNIVERSITY CORPORATION HAMAMATSU UNIVERSITY SCHOOL OF MEDICINE, Shizuoka (JP)

( * ) Notice: Subject to any disclaimer, the term of this patent is extended or adjusted under 35 U.S.C. 154(b) by 154 days.

(21) Appl. No.: 16/078,283

(22) PCT Filed: Feb. 10, 2017

(86) PCT No.: PCT/JP2017/005007
§ 371 (c)(1),
(2) Date: Aug. 21, 2018

(87) PCT Pub. No.: WO2017/145825
PCT Pub. Date: Aug. 31, 2017

(65) Prior Publication Data
US 2019/0051408 A1 Feb. 14, 2019

(30) Foreign Application Priority Data
Feb. 22, 2016 (JP) ................... 2016-030899
Feb. 22, 2016 (JP) ................... 2016-030900
(Continued)

(51) Int. Cl.
*A61B 34/00* (2016.01)
*G16H 40/40* (2018.01)
(Continued)

(52) U.S. Cl.
CPC ............. *G16H 40/40* (2018.01); *A61B 34/25* (2016.02); *A61B 50/30* (2016.02); *A61B 50/33* (2016.02);
(Continued)

(58) Field of Classification Search
CPC ............. A61L 2202/14; A61L 2202/17; A61L 2202/24; A61L 2/24; G06Q 10/00;
(Continued)

(56) References Cited

U.S. PATENT DOCUMENTS

2003/0170901 A1* 9/2003 Kippenhan ............... A61L 2/24
436/1
2004/0111012 A1* 6/2004 Whitman ........... A61B 1/00135
600/179
(Continued)

FOREIGN PATENT DOCUMENTS

JP 2003-078283 A 3/2003
JP 2003-111772 A 4/2003
(Continued)

OTHER PUBLICATIONS

Official Communication issued in International Patent Application No. PCT/JP2017/005007, dated Apr. 18, 2017.
(Continued)

*Primary Examiner* — George Manuel
(74) *Attorney, Agent, or Firm* — Keating & Bennett, LLP

(57) ABSTRACT

A medical tool work support system, a medical tool work support method, and a medical tool work support program alleviate a workload on a user. The medical tool work support system includes a display, a memory that stores data indicating a work procedure on a medical tool in a work step to be performed for surgery using the medical tool, and a
(Continued)

display controller that causes the display to display the work procedure based on the data stored in the memory.

14 Claims, 18 Drawing Sheets

(30) Foreign Application Priority Data

Feb. 22, 2016 (JP) ................................ 2016-030901
Feb. 22, 2016 (JP) ................................ 2016-030902

(51) Int. Cl.
| | | |
|---|---|---|
| A61L 2/24 | (2006.01) | |
| G06Q 10/00 | (2012.01) | |
| A61B 50/30 | (2016.01) | |
| G06Q 10/10 | (2012.01) | |
| G16H 20/40 | (2018.01) | |
| G16H 40/20 | (2018.01) | |
| A61B 90/98 | (2016.01) | |
| G16H 40/63 | (2018.01) | |
| A61B 50/33 | (2016.01) | |
| A61B 90/70 | (2016.01) | |
| A61B 90/90 | (2016.01) | |

(52) U.S. Cl.
CPC .............. *A61B 90/70* (2016.02); *A61B 90/90* (2016.02); *A61B 90/98* (2016.02); *A61L 2/24* (2013.01); *G06Q 10/00* (2013.01); *G06Q 10/10* (2013.01); *G16H 20/40* (2018.01); *G16H 40/20* (2018.01); *G16H 40/63* (2018.01); *A61B 2090/702* (2016.02); *A61L 2202/14* (2013.01); *A61L 2202/17* (2013.01); *A61L 2202/24* (2013.01)

(58) Field of Classification Search
CPC ........ G06Q 10/10; G16H 20/40; G16H 40/20; G16H 40/40; G16H 40/63; A61B 2090/702; A61B 34/25; A61B 50/30; A61B 50/33; A61B 90/70; A61B 90/90; A61B 90/98
See application file for complete search history.

(56) References Cited

U.S. PATENT DOCUMENTS

| | | |
|---|---|---|
| 2006/0059018 A1 | 3/2006 | Shiobara et al. |
| 2014/0263633 A1 | 9/2014 | Schmucker et al. |
| 2016/0212577 A1* | 7/2016 | Dor ..................... G06F 16/2379 |

FOREIGN PATENT DOCUMENTS

| | | |
|---|---|---|
| JP | 2005-237586 A | 9/2005 |
| JP | 2006-172336 A | 6/2006 |
| JP | 2006-178919 A | 7/2006 |
| JP | 2008-054732 A | 3/2008 |
| JP | 2012-215990 A | 11/2012 |
| JP | 2015-197735 A | 11/2015 |

OTHER PUBLICATIONS

Hamamatsu University School of Medicine, "Medical Photonics o Kiban to suru Hamamatsu Iko Renkei Kyoten Model", Mar. 13, 2015, pp. 1-11.
Ministry of Economy, Trade and Industry, "Hyoka Shihyo ni Motozuku Sangaku Renkei Kino Bunseki", retrieved on Apr. 6, 2017, 4 pages.
English translation of Official Communication issued in corresponding International Patent Application No. PCT/JP2017/005007, dated Aug. 28, 2018.

\* cited by examiner

MEDICAL TOOL WORK SUPPORT SYSTEM, MEDICAL TOOL WORK SUPPORT METHOD, AND MEDICAL TOOL WORK SUPPORT PROGRAM

CROSS REFERENCE TO RELATED APPLICATIONS

This application claims the benefit of priority to Japanese Patent Application No. 2016-030899 filed on Feb. 22, 2016, Japanese Patent Application No. 2016-030900 filed on Feb. 22, 2016, Japanese Patent Application No. 2016-030901 filed on Feb. 22, 2016, and Japanese Patent Application No. 2016-030902 filed on Feb. 22, 2016. The entire contents of each of these applications are hereby incorporated herein by reference.

BACKGROUND OF THE INVENTION

1. Field of the Invention

The present invention relates to a medical tool work support system, a medical tool work support method, and a medical tool work support program for supporting a work on a medical tool.

2. Description of the Related Art

Management systems for managing inventory and disinfection of surgical instruments and the like have been used to date. Japanese Patent Application Publication No. 2005-237586, for example, discloses a management system that manages inventory of reusable surgical instruments. In this management system, the reusable surgical instruments are assigned identification marks, and based on the identification marks, a database is created. The number of uses of each surgical instrument is counted so that surgical instruments whose counted numbers exceed the upper limits of useful life are discarded or replaced.

Japanese Patent Application Publication No. 2008-54732, for example, discloses a disinfection management system that inhibits the use of a used surgical instrument such as an endoscope, that is, a disinfection target that needs disinfection after surgery, if the disinfection target has not been cleaned or disinfected yet. This management system manages an endoscope provided with an IC tag that is transmissible and data-rewritable. When cleaning of the endoscope with an endoscope cleaning device, for example, is finished, information indicating a cleaned state and information indicating a cleaning date are written in an IC tag on this endoscope. Then, in using the endoscope, information stored in the IC tag of the endoscope can be read out with an IC tag reader. At this time, if the endoscope is determined to have not been cleaned yet based on the read-out information, inhibition of use of the endoscope is displayed on a monitor. With such a method, the use of an uncleaned endoscope is inhibited during surgery.

SUMMARY OF THE INVENTION

Examples of works on a medical tool such as a surgical instrument include cleaning in a state where the medical tool is disassembled into parts, assembly after the cleaning, and sterilization after the assembly. An operator conducts a work while referring to description and photographs on a work instruction manual. In a conventional work instruction manual, however, a part of a work procedure is omitted or points to be noticed are difficult to find. Thus, it takes time for understanding details of the work, which has been a heavy burden on a user.

Preferred embodiments of the present invention provide medical tool work support systems, medical tool work support methods, and medical tool work support programs that alleviate a workload on a user.

A medical tool work support system according to a preferred embodiment of the present invention is a medical tool work support system that supports a work on a medical tool in a work step with the medical tool. The work step is a step to be performed for surgery using the medical tool. The step to be performed for surgery includes at least one of the step of collecting the medical tool after the surgery, the step of cleaning the medical tool after the surgery, the step of assembling the medical tool after the cleaning, the step of sterilizing the medical tool after the assembly, and the step of storing the medical tool after the sterilization. The system includes a display, a memory that stores data indicating a work procedure on the medical tool in the work step, and a display controller that causes the display to display the work procedure based on the data stored in the memory. The work procedure includes not only a work that is performed in contact with a medical tool but also includes a work that is performed without contact the medical tool (e.g., a check work).

In a medical tool work support system according to a preferred embodiment of the present invention, details of a work procedure in a work step to be performed for surgery are displayed on the display. Accordingly, a user is able to sequentially understand details of tasks to be carried out in the work step. In this manner, unlike a conventional system, in a preferred embodiment of the present invention, omission of a part of the steps in the work procedure does not occur, and difficulty in finding points to be noticed in a work resulting from such omission does not occur, either. For example, in the case of inserting a first part of a medical tool into a second part of the medical tool and then positioning the first portion, a conventional work instruction manual has difficulty in finding which portion of the first part is to be inserted into the second part and in which portion of the second part the first part is to be inserted. On the other hand, in a preferred embodiment of the present invention, a series of work procedures to insert a predetermined portion of the first part into a predetermined portion of the second part, that is, a procedure from before the insertion to after the insertion, for example, is displayed. Accordingly, it does not take a long time for the user to understand the details of work procedures. As a result, a workload on the user is alleviated.

According to preferred embodiments of the present invention, medical tool work support systems, medical tool work support methods, and medical tool work support programs that alleviate a workload on a user are provided.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

First Preferred Embodiment

Figure 1:
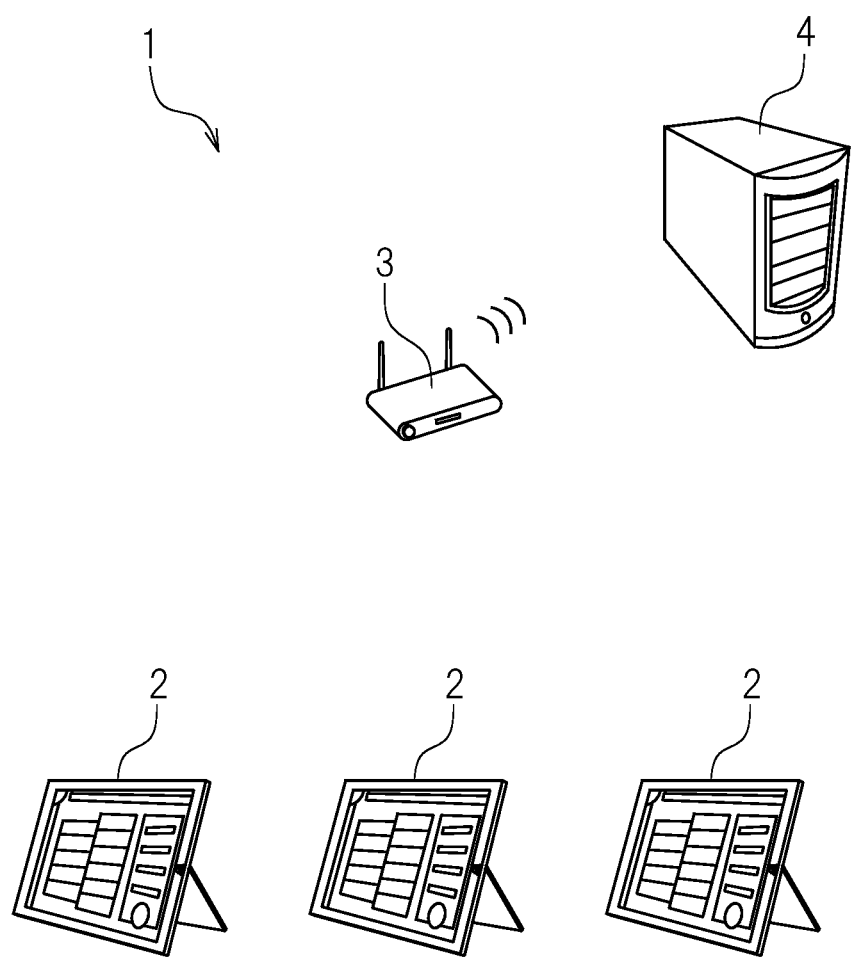
FIG. 1 is a schematic view illustrating a medical tool work support system according to a preferred embodiment of the present invention.

A medical tool work support system 1 according to a preferred embodiment of the present invention will be described hereinafter. As illustrated in FIG. 1, the medical tool work support system 1 includes a plurality of user terminals 2, an antenna 3, and a server 4. One of the plurality of user terminals is used by a manager. Although three user terminals 2 are provided in FIG. 1, the number of user terminals 2 in the medical tool work support system 1 may be one, two, or four or more. The user terminals 2 are devices that transmit and receive information to and from the antenna 3 wirelessly, such as personal computers, smartphones, or tablet terminals, for example. In this preferred embodiment, tablet terminals which are able to be easily carried by a user and including a display that is able to be easily seen are preferably used as the user terminals 2. In the following exemplary description, the user terminals 2 are tablet terminals. The user terminals 2 may communicate with the antenna 3 by wires, for example. The antenna 3 is connected to the server 4 through a local area network (LAN), for example. The server 4 stores various types of information concerning works on medical tools. The user terminals 2 transmit and receive information to and from the server 4 through the antenna 3.

In a case where a user conducts a work step on a medical tool, such as a work step of cleaning or assembly of the medical tool, the medical tool work support system 1 according to this preferred embodiment shows a work procedure of the work step and supports the user in accordance with the ability, that is, the skill, of the user. Work support by the medical tool work support system 1 according to this preferred embodiment will now be specifically described.

Figure 2:
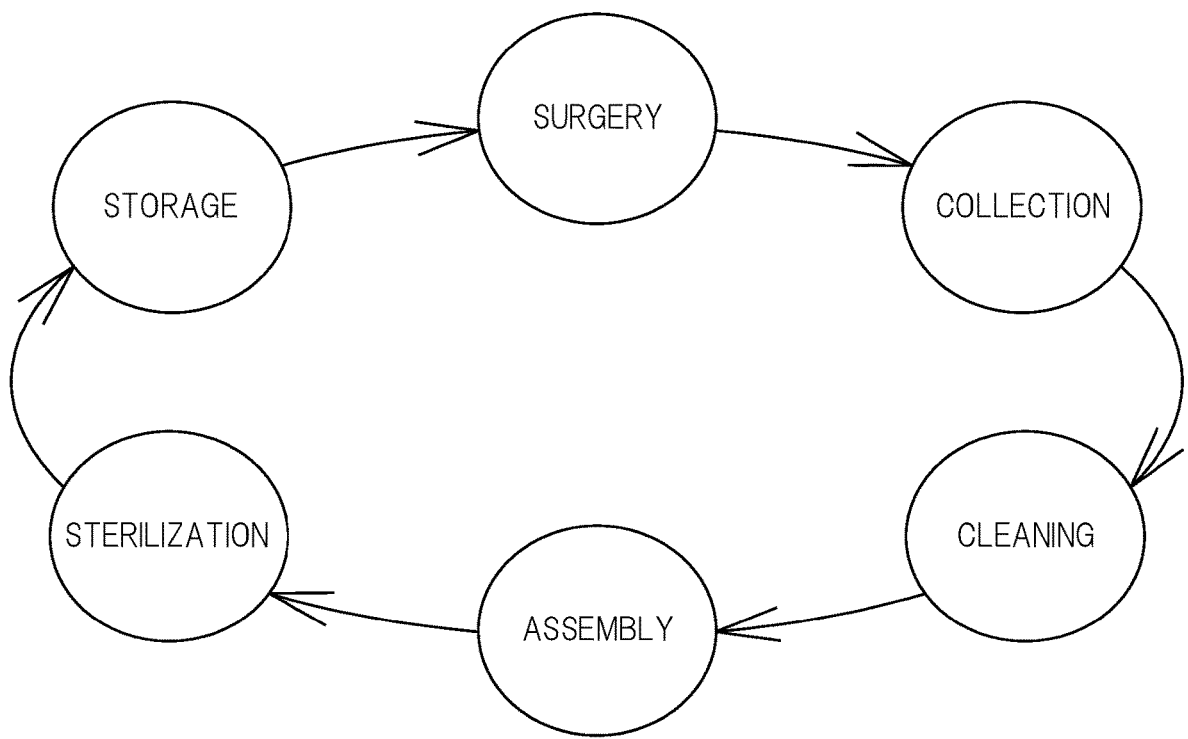
FIG. 2 is an illustration of a medical work step to which a medical tool work support system according to a preferred embodiment of the present invention is applied.

First, a work step (hereinafter referred to as a medical work step) using the medical tool work support system 1 will be described. The medical work step is a work step that is carried out for a surgery step using medical tools. Examples of the medical tools include clamps, surgical scissors, scalpels, scalpel holders, cannulae, forceps, retractors, scales, probes, elevators, raspatories, siphons, rib spreaders, rib contractors, needle holders, injectors, metal bowls, kidney basins, cups, pins, mirrors, files, mouth gags, clamps, handpieces, elevators (elepatriums), chisels, osteotrites, raspatories, mirrors, suture needles, punch (stanze), water receiving basins, needles, (tongue) pressors, bougies, vent pipes, bone impactors, luer rongeurs, radio pliers, hammers, goniometers, fraises, droppers, metal swabs, enemators, and syringes. These examples are only a portion of the medical tools, and the medical tools are not limited to these examples. As illustrated in FIG. 2, the medical work step includes, for example, five steps for the surgery step. Specifically, the medical work step includes a collection step, a cleaning step, an assembly step, a sterilization step, and a storage step, for example. The collection step is the step of collecting a medical tool after surgery. The cleaning step is the step of cleaning the collected medical tool after surgery in a disassembled state with a cleaning device. The assembly step is the step of assembling the medical tool after the cleaning. The sterilization step is the step of sterilizing the medical tool after the assembly. The storage step is the step of storing the sterilized medical tool for surgery. The medical tool work support system 1 is used in at least one of the five steps of the medical work step.

Figure 3:
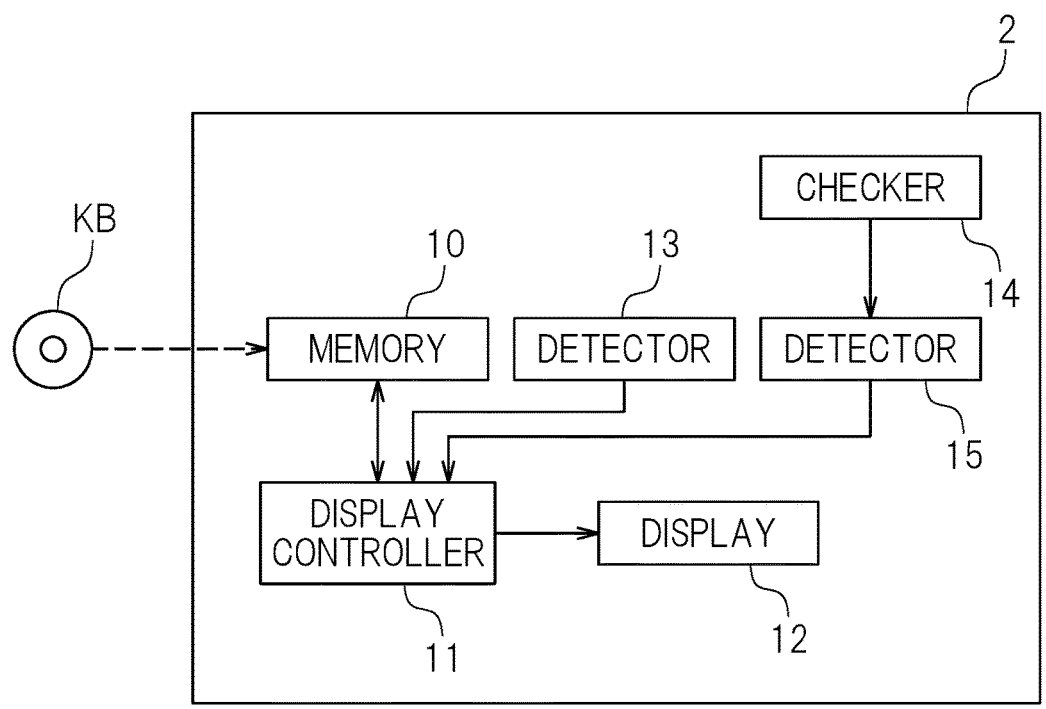
FIG. 3 is a block diagram illustrating a configuration of a user terminal according to a preferred embodiment of the present invention.

As illustrated in FIG. 3, each of the user terminals 2 (see FIG. 1) of the medical tool work support system 1 includes a memory 10, a display controller 11, a display 12, a detector 13, a checker 14, and a detector 15. The memory 10 can be implemented by a hard disk or a memory, for example. The display controller 11, the detector 13, the checker 14, and the detector 15 can be implemented by, for example, a central processing unit (CPU) provided in a known personal computer, a general-purpose computer, a tablet terminal, or the like, and a read only memory (ROM) and a random access memory (RAM) storing, for example, programs to be executed by the CPU, and so forth. The ROM stores a program or programs for causing processes on medical tools to be performed. The programs are read from a recording medium KB such as a compact disc (CD) or a digital versatile disc (DVD), for example. The programs may also be downloaded through the Internet. The display 12 is, for example, a touch panel such as a tablet terminal. In a case where the user terminal 2 is a personal computer, the display 12 can be a display of the personal computer.

The memory 10 previously stores a photograph showing a work procedure to support a work on a medical tool, various types of data of an illustration and a video, and still image data of an illustration. The memory 10 stores main work data representing details of one or more main works included in the medical work step and detailed work data representing details of one or more detailed works of each of the main works. A main work is a major work in one medical work step. A detailed work is a detailed work necessary to complete a main work in one medical work step (e.g., a cleaning step). That is, a main work includes one or more detailed works, and when all the detailed works are completed, the main work to which these detailed works belong is completed. In other words, a detailed work is a work obtained by dividing a main work into detailed works. For example, the cleaning step (see FIG. 2) includes five main works: disassembly of a medical tool into parts; arrangement of the parts of the medical tool on predetermined places of a tray; placement of the tray in a cleaning device; cleaning with the cleaning device; and drying of the parts after the cleaning. Examples of detailed works will be described. Examples of detailed works of a main work of disassembling a medical tool into parts include three tasks: disassembly of a first member of the medical tool; disassembly of a second member of the medical tool; and disassembly of a third member of the medical tool. The display controller 11 is configured or programmed to cause the display 12 to display the data indicating a work procedure stored in the memory 10. The detector 13, the checker 14, and the detector 15 will be described in detail later.

Figure 4:
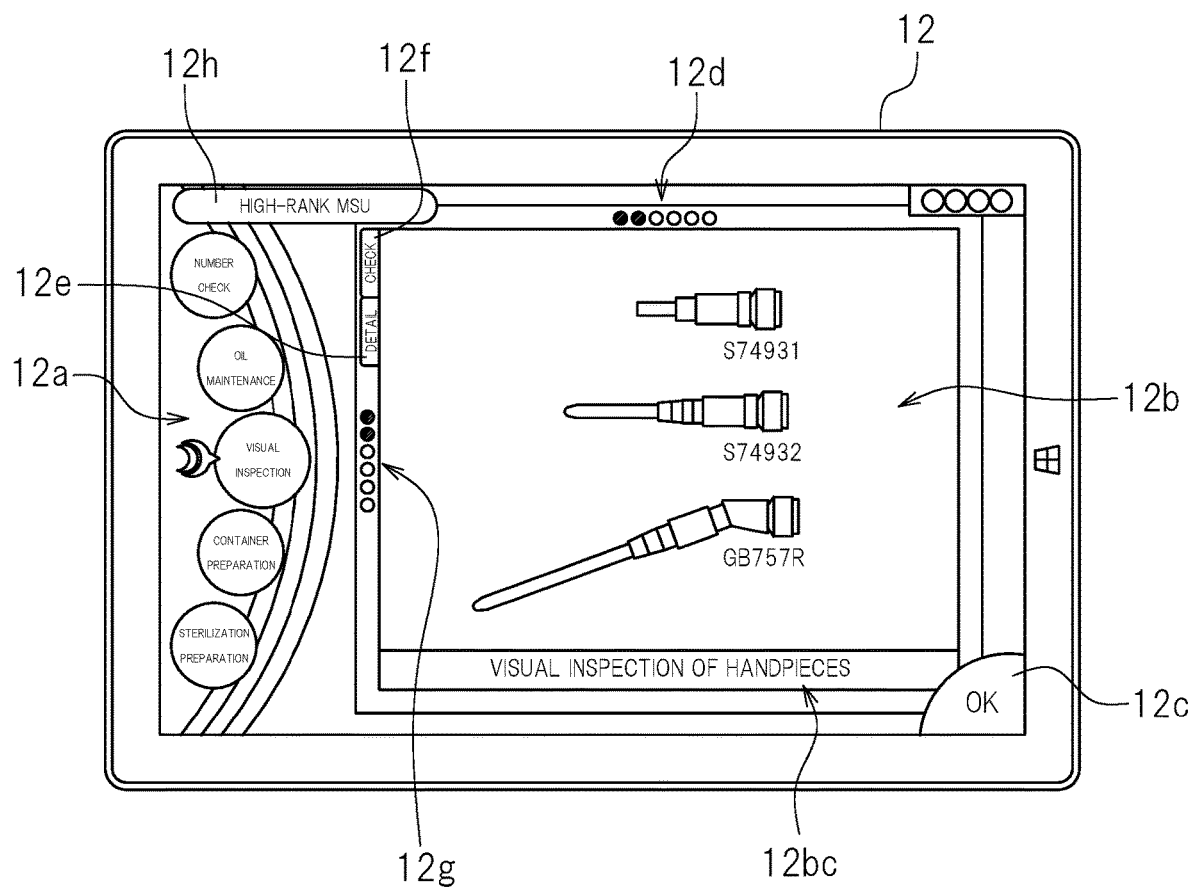
FIG. 4 is a view illustrating a touch panel of a user terminal according to a preferred embodiment of the present invention.

An example of the display 12 will be described. The following example of the display 12 is merely an example, and is not intended to limit the present invention. As illustrated in FIG. 4, the display 12 includes display regions 12a, 12b, 12bc, 12c, 12d, 12e, 12f, 12g, and 12h. The display region 12a displays buttons indicating items of predetermined works on a medical tool in a predetermined medical work step (hereinafter referred to as work item buttons). The display region 12a displays details of a plurality of detailed works described later. The display region 12b displays details of a work on a medical tool by an image (i.e., a photograph, an illustration, or a video). The display region 12bc displays details of the work on the medical tool by a text. The display region 12bc is disposed below the display region 12b. For example, the display region 12b displays a photograph of three handpieces arranged side by side. The display region 12bc displays a text "visual inspection of handpieces," for example. In this manner, the display on the display region 12bc facilitates understanding of details displayed on the display region 12b. That is, the display on the display region 12b is linked to the display on the display region 12bc. In displaying a work item set as a quality priority work (details of a main work) on the display region 12b, the display region 12c displays a check button. A check button (corresponding to the checker 14 described later) displayed on the display region 12c is pressed by a user when the main work set as the quality priority work is completed. In this configuration, unless the check button is pressed, details of a main work at the next step are not displayed or a completion display indicating completion of the work is not provided. In this manner, the user has to conduct a work and check elaborately, and thus, quality of the main work set as the quality priority work is able to be assured. The detector 15 illustrated in FIG. 3 detects whether the checker 14 is pressed by the user or not. If the detector 15 detects pressing, the display controller 11 illustrated in FIG. 3 causes the display 12 to display details of a main work in the next step or to provide a completion display. In this configuration, when the user presses the check button, this information remains in the server 4 (see FIG. 1) as a history, and the manager is able to easily access the server 4 to find that quality priority management (also called gate management) was conducted by the user without fail.

The display region 12d displays the page number of one or more steps included in one work item. The display region 12d displays the page number of a current main work in a plurality of main works included in one medical work step. The display region 12e displays a text "detail," for example, in a case where a detailed work is set as a current main work. Accordingly, the user is able to recognize that details of the detailed work can be displayed. Then, as will be described later, the user moves a finger with the fingertip being in contact with the display 12 (where this operation is generally called a "flick") so that details of the detailed work can be displayed. In a case where the user uses a personal computer as the user terminal 2, a button to be pressed when the user visually recognizes details of a detailed work may be disposed on the display region 12e. In this manner, whether details of the detailed work are displayed or not is determined by selection by the user. In this case, details of the detailed work may be displayed by a beginner user or even by an experienced user who wants to carefully check detailed works. The detector 13 illustrated in FIG. 3 detects whether a flick has been performed on the display region 12b by the user or not. If the flick is detected by the detector 13, the display controller 11 illustrated in FIG. 3 causes the display 12 to provide a display indicating details of a detailed work. The display region 12g displays the total number of detailed works included in a main work, also displays the page number of a detailed work currently displayed on the display region 12b. For example, in a case where the total number of detailed works is six and the page number of a detailed work currently displayed on the display region 12b is the second page, two of six blank circles are filled in display. Accordingly, the user is able to clearly understand the total number of detailed works included in a specific main work and the page number of a detailed work currently displayed. The display region 12f displays a mark indicating the quality priority work described above. The display region 12h displays a button to finish medical tool work support system 1. When the user intends to finish the medical tool work support system 1, the user presses the button on the display region 12h.

Figure 5A:
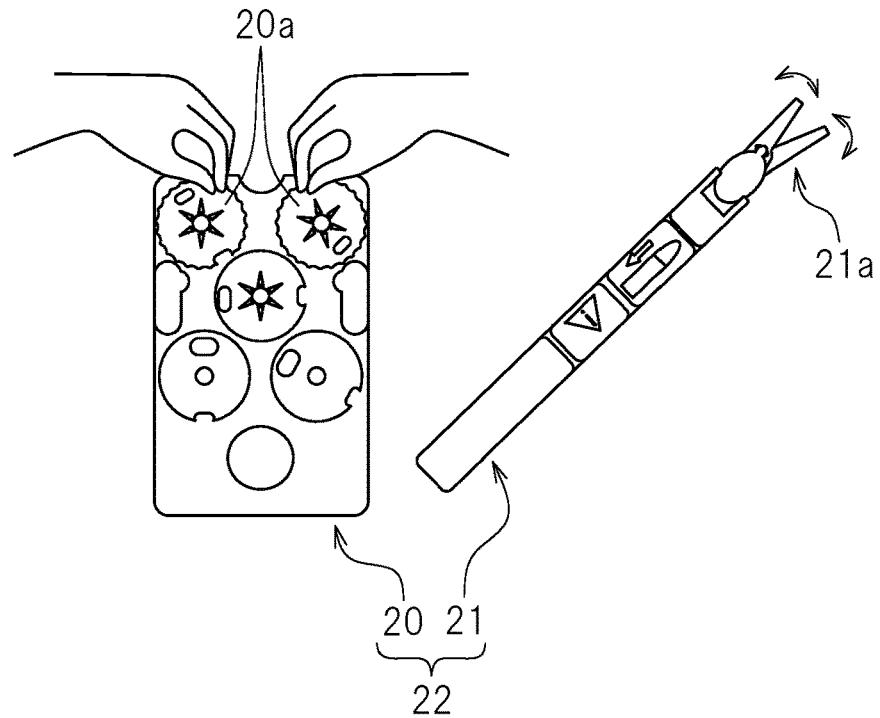
FIG. 5A is an illustration of a fragment image of a video of a work procedure on a medical tool displayed on a user terminal according to a preferred embodiment of the present invention.
Figure 5B:
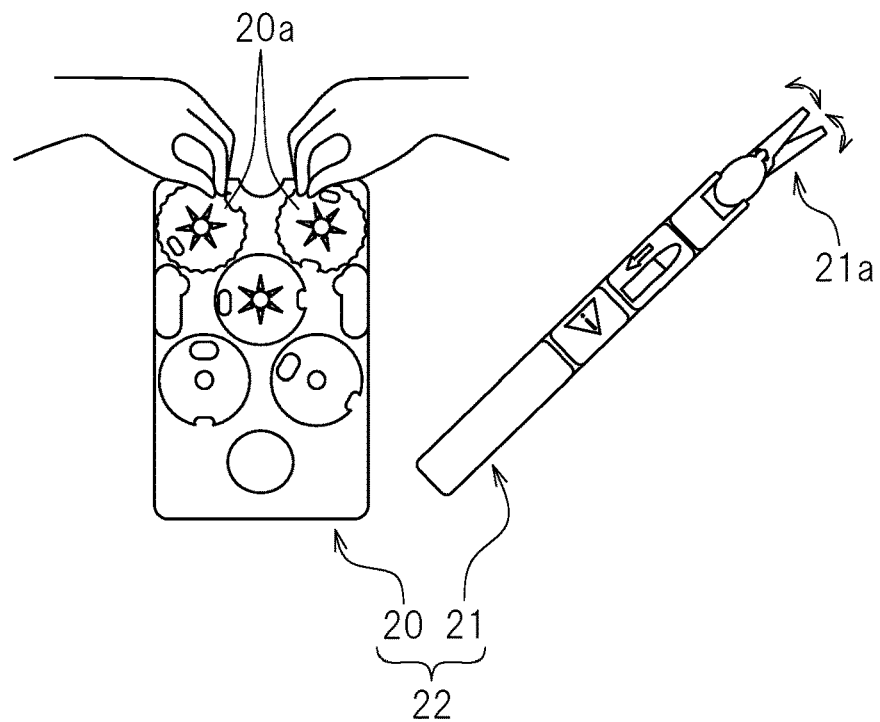
FIG. 5B is an illustration of a fragment image of a video of a work procedure on the medical tool displayed on a user terminal according to a preferred embodiment of the present invention.

A known example of the medical tool is an electric clamp illustrated in FIG. 5A. The electric clamp 22 includes a manipulator 20 and a clamp element 21 including a holding portion 21a that moves in conjunction with an operation of the manipulator 20 by the user. The manipulator 20 is a remote controller that issues an instruction from a remote place to the clamp element 21 to an unillustrated controlling portion of the clamp element 21. The manipulator 20 includes a pair of dials 20a. The user turns the dials 20a of the manipulator 20 to cause the holding portion 21a of the clamp element 21 to pivot. FIG. 5A illustrates a state where the holding portion 21a is open, whereas FIG. 5B illustrates a state where the holding portion 21a is closed. The memory 10 (see FIG. 3) stores video data representing a state where the dials 20a of the manipulator 20 are turned by the user and a state where the holding portion 21a is opened and closed in conjunction with the turning of the dials 20a. When a predetermined work item button on the display region 12a (see FIG. 4) is pressed by the user, the display controller 11 (see FIG. 3) displays a video including the images illustrated in FIGS. 5A and 5B on the display region 12b of the display 12. The user visually recognizes the display 12 to easily understand a link between the direction in which the dials 20a are turned to opening and closing of the holding portion 21a.

Figure 6:
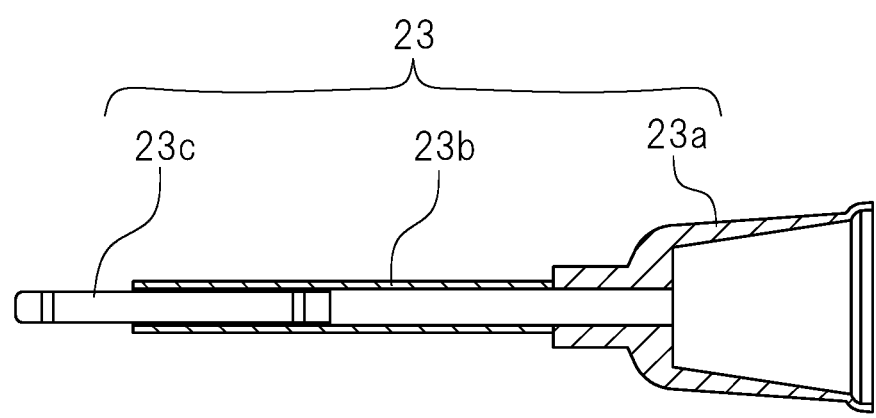
FIG. 6 is a cross-sectional view illustrating a configuration of a handpiece according to a preferred embodiment of the present invention.
Figure 7A:
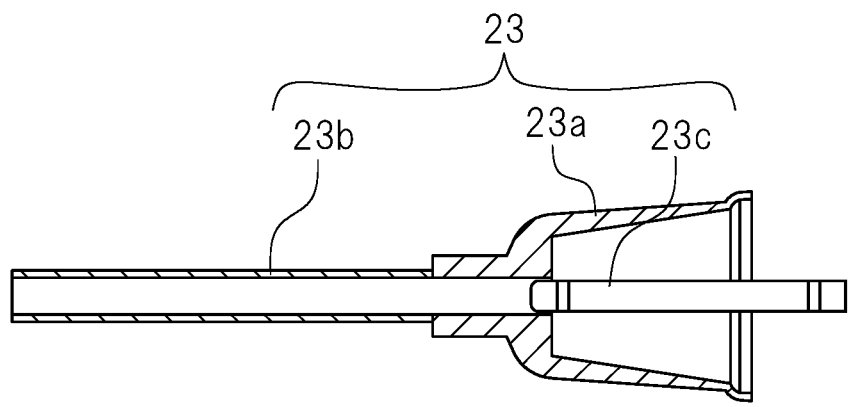
FIG. 7A is a view illustrating a fragment image of a video of an insertion procedure of a pin in a handpiece displayed on a user terminal according to a preferred embodiment of the present invention.
Figure 7B:
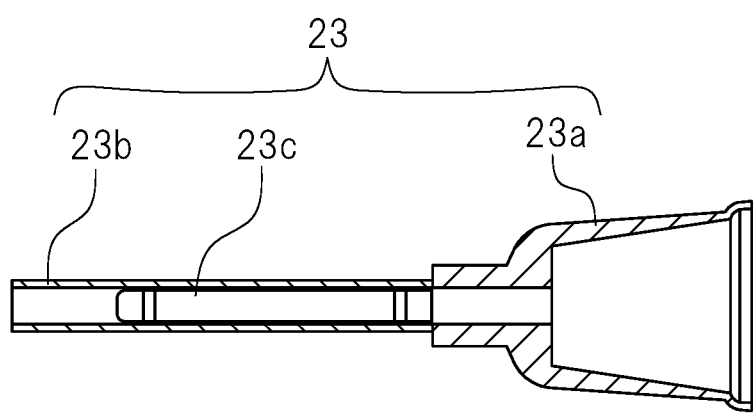
FIG. 7B is a view illustrating a fragment image of the video of the insertion procedure of the pin in the handpiece displayed on a user terminal according to a preferred embodiment of the present invention.
Figure 7C:
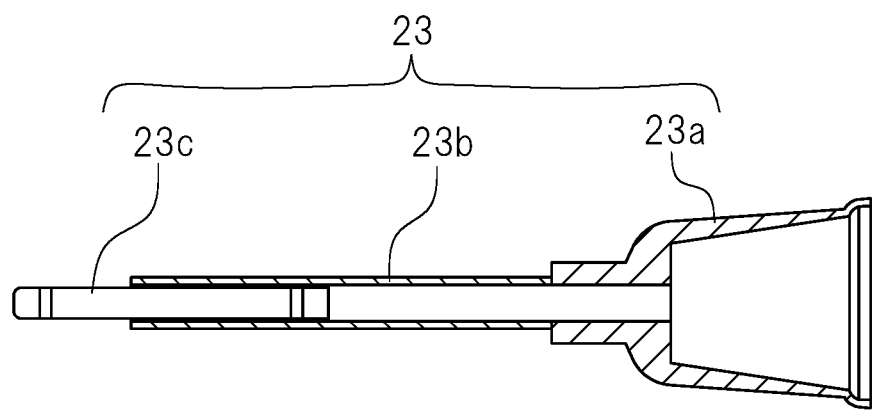
FIG. 7C is a view illustrating a fragment image of the video of the insertion procedure of the pin in the handpiece displayed on a user terminal according to a preferred embodiment of the present invention.

The display 12 may also display a video as follows. A known example of the medical tool is a handpiece 23 illustrated in FIG. 6. The handpiece 23 includes a first pipe portion 23a; a second pipe portion 23b coaxially disposed with the first pipe portion 23a, having a diameter smaller than that of the first pipe portion 23a, and extending linearly, and a pin 23c inserted and positioned in the second pipe portion 23b so that a distal end portion of a pin 23c projects. The memory 10 (see FIG. 3) stores video data indicating a state where the pin 23c is inserted into the first pipe portion 23a and the second pipe portion 23b in this order. That is, the video data is data representing a positioning procedure indicating a flow of positioning of the pin 23c relative to the second pipe portion 23b. When the user presses a predetermined work item button on the display region 12a (see FIG. 4), the display controller 11 (see FIG. 3) causes the display region 12b of the display 12 to display a video including images illustrated in FIGS. 7A, 7B, and 7C. The user visually recognizes the display 12 to easily understand an insertion method and a positioning procedure of the pin 23c.

Figure 8:
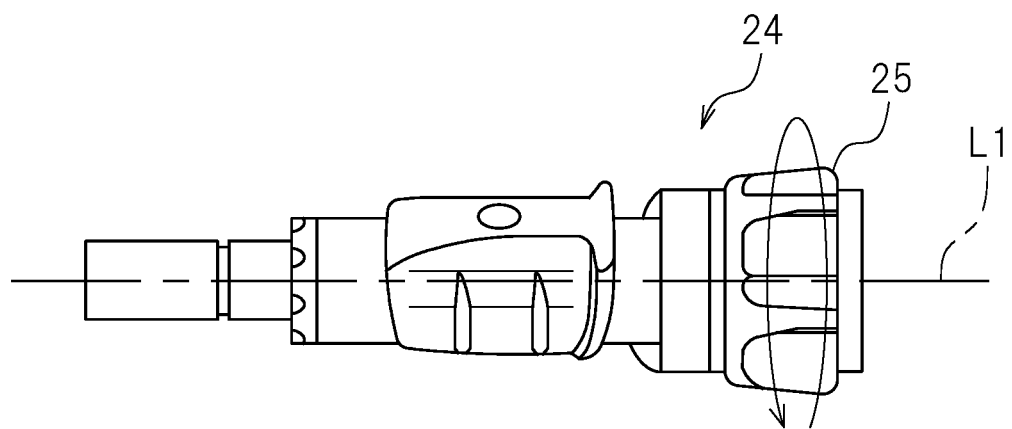
FIG. 8 is a fragment image of a video of a medical tool displayed on a user terminal according to a preferred embodiment of the present invention.

The display 12 may also display a video as follows. FIG. 8 is a view illustrating a partial detail of a medical tool. As illustrated in FIG. 8, the medical tool 24 includes a rotary member 25 that rotates about a center axis L1. The memory 10 (see FIG. 3) stores video data indicating a state where the rotary member 25 rotates. When a predetermined work item button on the display region 12a (see FIG. 4) is pressed by the user, the display controller 11 (see FIG. 3) displays a video including the image illustrated in FIG. 8 on the display region 12b of the display 12. The user visually recognizes the display 12 to easily understand that the rotary member 25 rotates.

As described above, in this preferred embodiment, details of a work procedure in a work step carried out for surgery are displayed on the display 12. Accordingly, the user is able to sequentially understand details of works to be carried out in the work step. In this manner, unlike a conventional system, in this preferred embodiment, omission of a part of the steps in the work procedure does not occur, and difficulty in finding points to be noticed in a work resulting from such omission does not occur, either. In the case of conducting a work of inserting a first portion of a medical tool into a second portion of the medical tool and then positioning the first portion, for example, a conventional work instruction manual has difficulty in finding which portion of the first portion is to be inserted in the second portion and in which portion of the second portion the first portion is to be inserted. On the other hand, in the medical tool work support system according to this preferred embodiment, a series of work procedures to insert a predetermined portion of the first portion in a predetermined portion of the second portion, that is, a procedure from before the insertion to after the insertion, for example, is displayed. Accordingly, it does not take a long time for the user to understand details of a work. As a result, a workload on the user is alleviated.

In addition, in this preferred embodiment, details of a work procedure in a work step carried out for surgery are displayed by a video. Accordingly, a flow of a series of the work procedures is able to be easily displayed. As a result, the user is able to easily understand details of the work.

Furthermore, in this preferred embodiment, details of the positioning procedure of the medical tool is displayed by a video. Accordingly, the user is able to easily understand the positioning procedure of the medical tool. In the example described above, the user is able to easily understand how to insert the pin 23c, that is, the method of inserting the pin 23c in the first pipe portion 23a and then the second pipe portion 23b.

Moreover, in this preferred embodiment, details of the work procedure on the medical tool are displayed by an illustration video. Accordingly, the user is able to easily understand the work procedure. In the example described above, the user is able to easily understand that the holding portion 21a can be opened by turning the dials 20a of the manipulator 20 in one direction and the holding portion 21a can be closed by turning the dials 20a in the opposite direction.

In this preferred embodiment, since a video is created by an illustration, even in a case where it is difficult to create a video by an actual shooting, for example, in a case where the pin 23c is inserted in the first pipe portion 23a and the second pipe portion 23b in this order, a video indicating a work procedure is able to be easily prepared. The use of an illustration enables a video to be created with omission of a portion of a medical tool not significantly related to a work procedure. Thus, the user is able to easily focus on a display and easily understand the work procedure.

In the preferred embodiment described above, a video of an illustration is displayed. The present invention, however, is not limited to this example, and a video created by actual shooting is able to be displayed. Instead of displaying a still image of an illustration, photograph data may be displayed.

A cross-sectional view and an enlarged view of a medical tool may be displayed by an illustration still image. For example, since it is relatively difficult to show an internal configuration of a medical tool by a photograph, the internal configuration is able to be displayed using a cross-sectional view of an illustration in such a case. To facilitate understanding of the internal configuration of the medical tool, the internal configuration may be displayed using an enlarged view of an illustration.

Second Preferred Embodiment

Next, display examples of main works and detailed works in a display 12 according to a second preferred embodiment of the present invention will be described with reference to FIG. 9. The main works and detailed works in a medical work step will be displayed as follows, for example. As indicated by character A in FIG. 9, the display region 12b of the display 12 displays, as details of the first main work, a photograph indicating a state where medical tools are randomly placed on an upper tray and a lower tray, for example. The display region 12bc of the display 12c displays a text "place medical tools on upper and lower trays" in, for example, white. On the display region 12bc, the background color of the text is set in, for example, blue. The background color of the display region 12bc displaying details of subsequent main works are also set in blue except for a case where a quality priority work is set. While visually recognizing the display 12, the user conducts a work of placing a plurality of medical tools on the upper tray and the lower tray at random. Once the work is completed, the user touches the display region 12b and flicks a finger to the left (i.e., to the left on the drawing sheet), for example. Accordingly, the display region 12b is allowed to display details of a main work at the next step (i.e., a work indicated by character B in FIG. 9 described later). On the other hand, by flicking the finger to the right (i.e., to the right on the drawing sheet) from the above-described state, the user is able to make the display region 12b display details of the main work at the first step. In this manner, the user is able to make the display region to display details of the main work at the next step by flicking the finger to the left, and to return to the display of the main work at the previous step by flicking the finger to the right.

Subsequently, as indicated by character B in FIG. 9, the display region 12b displays a photograph indicating a state where predetermined medical tools are arranged at predetermined places on the lower tray. The predetermined medical tools are, for example, a handpiece or a motor. The predetermined medical tools, however, are not limited to these examples. The display region 12bc displays a text "completion of preparation of tools on the lower tray." In this case, while visually recognizing the display 12, the user conducts a work of arranging predetermined medical tools at predetermined places on the lower tray.

Figure 9:
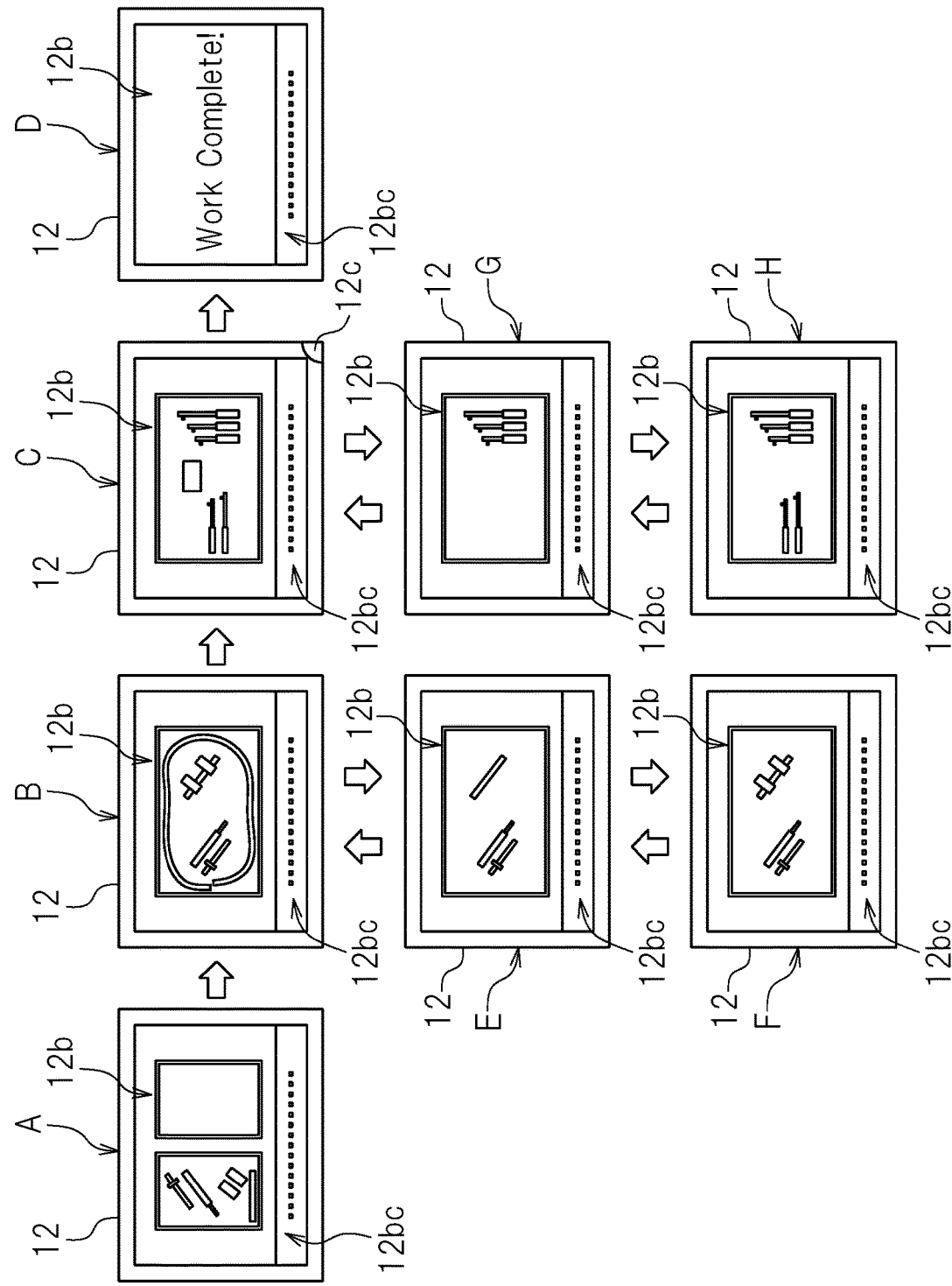
FIG. 9 is a schematic view of a display example indicating details of a main work and a detailed work by a display according to a preferred embodiment of the present invention.

Here, in a case where a detailed work is set for the main work indicated by character B in FIG. 9, the display region 12e displays a text "detail" as described above. Accordingly, the user is able to recognize that the currently displayed main work includes the detailed work. At this time, if the user wants to check the detailed work included in the main work indicated by character B in FIG. 9, the user touches the display region 12b in the state indicated by character B in FIG. 9 and flicks the finger upward (i.e., upward in the drawing sheet), for example. Accordingly, the display region 12b is allowed to display details of the detailed work. In this case, as indicated by character E in FIG. 9, the display region 12b displays a photograph indicating a state where two motors are arranged at predetermined places on the lower tray, for example. The display region 12bc displays a text such as "firmly place two motors at predetermined places" in, for example, white. On this display region 12bc, the background color of the text is set in green, for example. The background color of the display region 12bc displaying details of subsequent detailed works are also set in green. The background color of the display region 12bc displaying details of a detailed work only needs to be different from the background color of the display region 12bc displaying details of a main work, and is not limited to green. While visually recognizing the display 12, the user conducts a task of respectively placing the two motors at predetermined places on the lower tray.

As described above, the display region 12g displays the total number of detailed works included in a main work, and the page number of a detailed work currently displayed on the display region 12b. Based on the display of the display region 12g, the user is able to determine whether or not there is a detailed work yet to be displayed. If there is a detailed work yet to be displayed, the user performs a flick operation in a manner similar to that described above. Accordingly, the display region 12b is allowed to display details of a next detailed work. In this case, as indicated by character F in FIG. 9, the display region 12b displays a photograph indicating a state where two handpieces are arranged at predetermined places on the lower tray, for example. The display region 12bc displays a text such as "firmly place two handpieces at predetermined places." While visually recognizing the display 12, the user conducts a work of respectively placing the two handpieces at predetermined places on the lower tray.

Subsequently, a method to display details of a main work next to the main work indicated by character B in FIG. 9 will be described. As described above, since the display region 12d displays the page number of a current main work, the user is able to determine whether there is a main work yet to be displayed or not, based on the display of the display region 12d. Here, it is assumed that there is a main work next to the main work indicated by character B in FIG. 9. First, the user performs a flick operation twice downward from the state indicated by character F in FIG. 9 so that the display of the display region 12b returns to the display indicated by character B in FIG. 9. Then, the user performs a flick operation to the left from the state indicated by character B in FIG. 9. Accordingly, as indicated by character C in FIG. 9, details of the next main work are displayed on the display region 12b, and the user conducts a predetermined work. With respect to character C in FIG. 9, a check button indicating that the main work indicated by character C in FIG. 9 is the quality priority work described above is displayed on the display region 12c. The background color of the display region 12bc displaying details of the main work as the quality priority work is set in red, for example. The background color of the display region 12bc displaying details of the main work as the quality priority work only needs to be different from the background color of the display region 12bc displaying details of a main work and the background color of the display region 12bc displaying details of a detailed work, and is not limited to red. Although the states where details of detailed works of the main work indicated by character C in FIG. 9 are indicated by character G in FIG. 9 and character H in FIG. 9 are illustrated, the method to display these states and the method for returning the display to the display indicated by character C in FIG. 9 are the same as those described above, and description thereof will not be repeated.

Thereafter, the user returns the display on the display region 12b to the display indicated by character C in FIG. 9 by the same method as the method described above. The use then performs a flick operation to the left from the state indicated by character C in FIG. 9. Accordingly, as indicated by character D in FIG. 9, the display region 12b provides a completion display indicating that all the main works are completed, that is, one medical work step is completed. In a case where there is a main work next to the main work indicated by character C in FIG. 9, details of the next main work are displayed instead of the completion display indicated by character D in FIG. 9. The foregoing description is related to display examples of main works and detailed works. In a case where detailed works do not need to be checked, the user (e.g., an experienced user) sequentially performs a flick operation to the left so that the displays indicated by characters A, B, C, and D in FIG. 9, that is, only details of the main work, can be displayed. Even for a beginner user, checking for all the detailed works may be omitted similarly, or only a part of the detailed works may be checked.

As described above, in this preferred embodiment, details of a main work in a work step to be performed for surgery are displayed on the display 12, and details of a detailed work of the main work are selectively displayed on the display 12. That is, details of a detailed work may be displayed and may not be displayed. For example, details of a detailed work may not be displayed for an experienced user having a skill for the work, while being displayed for a beginner user who is not used to the work. In the manner described above, display and non-display for a detailed work is able to be selected depending on a work ability of a user, and thus, the need for a considerable time for reading all the details in a conventional redundant work instruction manual is eliminated. In the medical tool work support system 1 according to this preferred embodiment, for an experienced user, for example, display of a detailed work with which the experienced user is familiar and which is understood by the experienced user is able to be omitted. Even for a beginner user, display of a detailed work may be omitted depending on a work ability of the user. Accordingly, efficiency in a work on medical tools is increased. As a result, all possible preparations can be made for surgery for which a delay of preparation of medical tools is impermissible.

In addition, in this preferred embodiment, the background color of the display region 12bc displaying details of a main work is set in blue, for example, and the background color of the display region 12bc displaying details of a detailed work is set in green. In this manner, the display region 12bc displaying details of a main work and the display region 12bc displaying details of a detailed work are represented by different colors so that an attention is attracted by a user, and the user is able to easily distinguish details of the main work from details of the detailed work.

In this preferred embodiment, the background color of the display region 12bc displaying details of the main work set as the quality priority work is set in red, for example. In this manner, the background color indicating the quality priority work is different from the background color indicating a normal main work (i.e., a main work except for the main work set as the quality priority work) and the background color indicating a detailed work, and thus, attention is attracted by a use so that the user is able to easily recognize that the current work is the quality priority work.

In this preferred embodiment, when the main work set as the quality priority work is finished, the user needs to press the check button on the display region 12c. In this configuration, unless the check button is pressed, details of a main work at the next step are not displayed or a completion display indicating completion of the work is not provided. In this manner, the user has to conduct work and check elaborately, and thus, quality of the main work set as the quality priority work is able to be assured.

In this preferred embodiment, details of a detailed work are displayed by a photograph based on photograph data on the display region 12b. In this manner, the display by the photograph provides reality to details of the detailed work. As a result, the user is able to easily understand details of the detailed work by visually comparing with actual medical tools.

In the preferred embodiment described above, although details of the detailed works are displayed by photographs, the present invention is not limited to this example. Details of detailed works may be displayed by videos. For example, in the assembly step (see FIG. 2) described above, in assembling a plurality of parts of a medical tool, a positioning procedure of one part relative to another part can be displayed by a video. Accordingly, the user is able to smoothly conduct the positioning work.

In the preferred embodiment described above, although details of the detailed works are displayed by photographs, the present invention is not limited to this example. The details of detailed works may be displayed by illustrations. For example, since it is relatively difficult to show an internal configuration of a medical tool by a photograph, the internal configuration may be displayed using a cross-sectional view of an illustration in such a case. The internal configuration may be displayed by an enlarged view of an illustration. In this manner, it can be determined which one of a photograph, a video, and an illustration, based on details of a work on a medical tool.

Although the foregoing description is directed to the medical tool work support system 1, the medical tool work support system 1 is not limited to the technical features described above, and can be implemented with the following variations.

In the preferred embodiment described above, tablet terminals are used as the user terminals 2, but the present invention is not limited to this example. As the user terminals 2, personal computers, smartphones, and so forth may also be used. In the case of using a personal computer, a user is able to switch display by operating a mouse while visually recognizing a display on a display device. Switching of the display in the case of using a smartphone is basically similar to the operation described above with the tablet terminal.

In addition, in the preferred embodiment described above, the medical work step includes at least one of the collection step, the cleaning step, the assembly step, the sterilization step, and the storage step, but may include another step except for these five steps. That is, the medical work step only needs to satisfy a condition that the medical work step is a step to be carried out for a surgery step.

Third Preferred Embodiment

Figure 10:
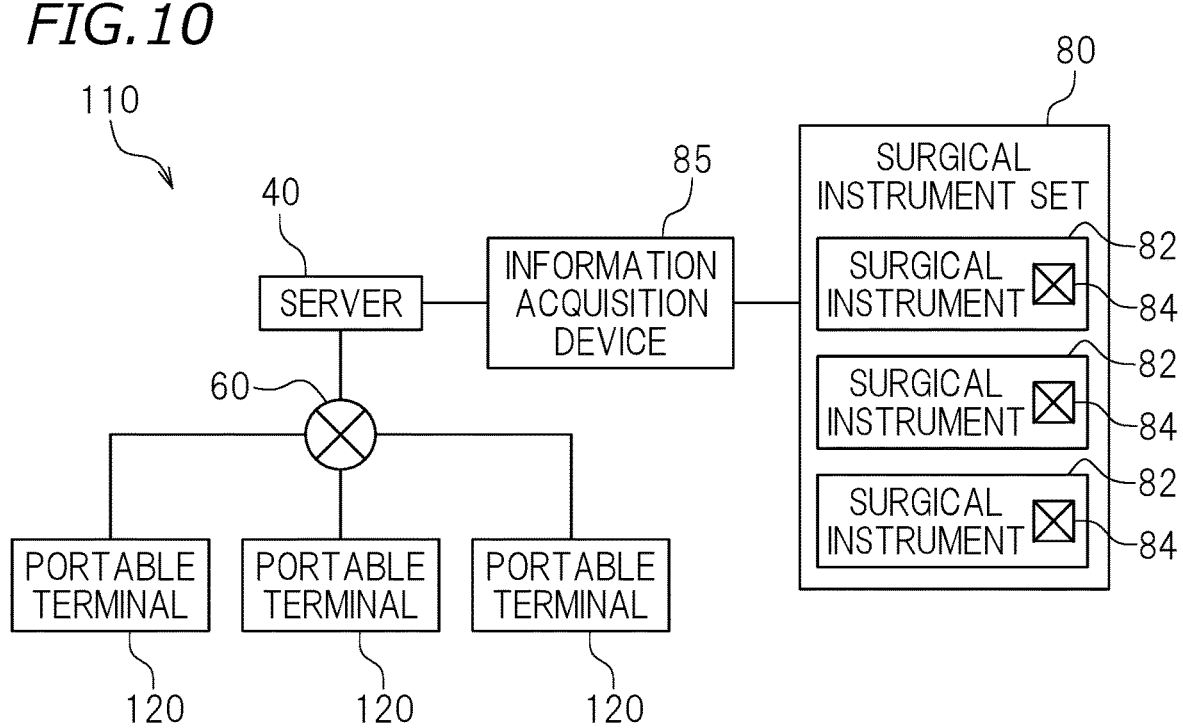
FIG. 10 is a schematic view illustrating a surgical instrument set management system according to a preferred embodiment of the present invention.

Next, a surgical instrument set management system according to a preferred embodiment of the present invention will be described. The surgical instrument set management system according to this preferred embodiment manages a change in surgical instrument sets each including a plurality of surgical instruments. As illustrated in FIG. 10, the surgical instrument set management system 110 includes a plurality of portable terminals 120, a server 40, and a network 60. The server 40 is a computer that provides service to the portable terminals 120 through the network 60. The server 40 is configured or programmed to enable communication with the plurality of portable terminals 120 through the network 60. The server 40 and the portable terminals 120 are configured or programmed to communicate with each other wirelessly. Examples of the portable terminals 120 include laptop personal computers, tablet terminals, and smartphones. The network 60 is not limited to a specific type, and may be the Internet or a local area network (LAN), for example.

Figure 11:
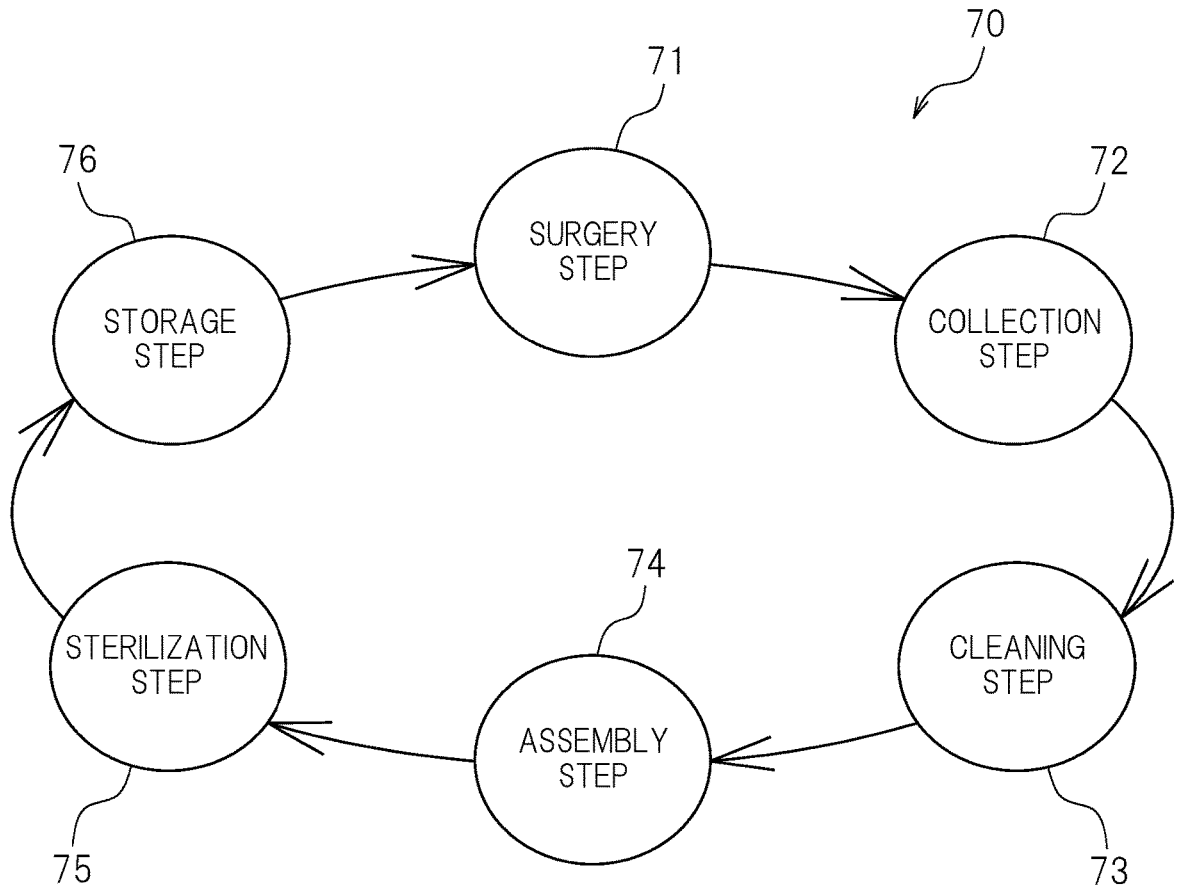
FIG. 11 is an illustration of a circulation cycle using a surgical instrument set management system according to a preferred embodiment of the present invention.

FIG. 11 is an illustration of a circulation cycle 70 in which the surgical instrument set management system 110 is used. As illustrated in FIG. 11, the circulation cycle 70 includes a surgery step 71, a collection step 72, a cleaning step 73, an assembly step 74, a sterilization step 75, and a storage step 76. In the circulation cycle 70, a surgical instrument set 80 (see FIG. 10) circulates in the order of the surgery step 71, the collection step 72, the cleaning step 73, the assembly step 74, the sterilization step 75, the storage step 76, and the surgery step 71. In the surgery step 71, surgery of a patient is conducted with the stored surgical instrument set 80. In the collection step 72, the surgical instrument set 80 used for surgery is collected. In the cleaning step 73, the collected surgical instrument set 80 is cleaned. In the assembly step 74, the cleaned surgical instrument set 80 is assembled. In the assembly step 74, surgical instruments 82 (see FIG. 10) individually cleaned in the cleaning step 73 are returned to a predetermined surgical instrument set 80. In the sterilization step 75, the assembled surgical instrument set 80 is sterilized. In the storage step 76, the sterilized surgical instrument set 80 is stored in predetermined storage space. Here, in the steps of the circulation cycle 70, some of the surgical instruments 82 in the surgical instrument set 80 are in short in some cases. For some types of surgery in hospital departments, surgery is able to be conducted without problems even when part of the surgical instrument set 80 is missing. Thus, in hospitals, even in a case where the surgical instrument set 80 has a change such as missing of instruments, works up to the storage step 76 are completed in preparation for surgery in the surgery step 71. The surgical instrument set management system 110 is used in at least one of the six steps included in the circulation cycle 70.

As illustrated in FIG. 10, the surgical instrument set 80 includes a plurality of surgical instruments 82. The surgical instrument set 80 widely varies among the types of surgery and doctors using the surgical instrument set 80. Here, the surgical instruments 82 included in the surgical instrument set 80 are similar to the medical tools described in the first preferred embodiment. Each of the surgical instruments 82 in the surgical instrument set 80 is provided with an identification unit 84. The identification unit 84 is associated with information of the surgical instrument set 80 including these surgical instruments 82. That is, in one surgical instrument set 80, information on this surgical instrument set 80 is the same among the identification units 84 of the surgical instruments 82.

As illustrated in FIG. 10, the surgical instrument set management system 110 includes an information acquisition device 85. The information acquisition device 85 acquires information of the identification units 84 of the surgical instruments 82. The information acquisition device 85 transmits information of the identification units 84 to the server 40. Examples of the information acquisition device 85 include an IC tag reader, and examples of the identification units 84 include an IC tag. The IC tag reader communicates with the IC tag wirelessly.

Figure 12:
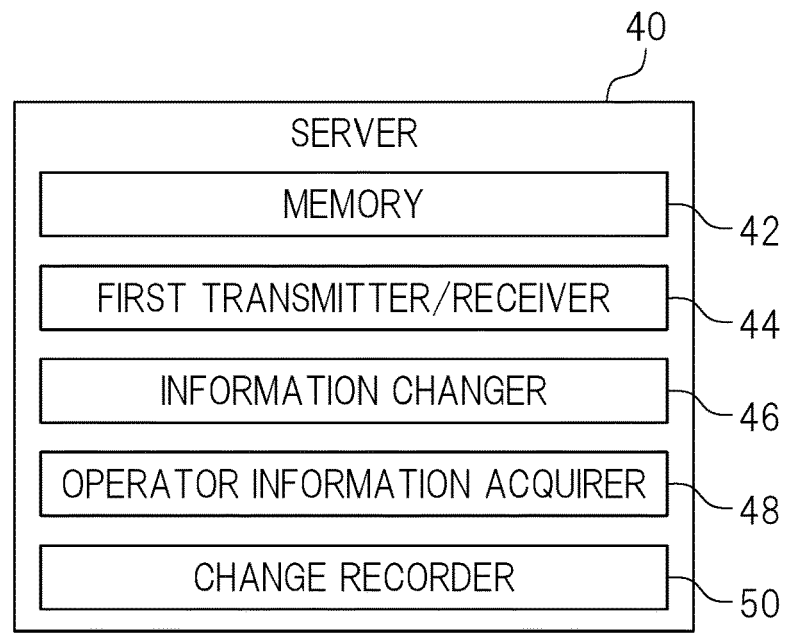
FIG. 12 is a block diagram illustrating a configuration of a server according to a preferred embodiment of the present invention.

As illustrated in FIG. 12, the server 40 is configured or programmed to include a memory 42, a first transmitter/receiver 44, an information changer 46, an operator information acquirer 48, and a change recorder 50.

The memory 42 stores information on the surgical instrument set 80 (see FIG. 10) including the plurality of surgical instruments 82 (see FIG. 10). The information on the surgical instrument set 80 is stored in the memory 42 beforehand. The memory 42 stores information on the surgical instrument set 80 updated by the changer 46. The memory 42 can be implemented by, for example, a hard disk or a memory. The information on the surgical instrument set 80 includes, for example, a photograph 80A displaying the surgical instrument set 80 (see FIG. 13), basic information on the surgical instrument set 80, and a memo concerning the surgical instrument set 80. The basic information of the surgical instrument set 80 includes, for example, information indicating to which hospital department the surgical instrument set 80 belongs, information indicating the name of the surgical instrument set 80, information indicating the number of surgical instruments 82 included in the surgical instrument set 80, information indicating a container for housing the surgical instrument set 80, and information indicating a sterilization method of the surgical instrument set 80.

The first transmitter/receiver 44 transmits and receives information on the surgical instrument set 80. More specifically, the first transmitter/receiver 44 transmits information on the surgical instrument set 80 to the portable terminals 120. The first transmitter/receiver 44 receives the changed information on the surgical instrument set 80 transmitted from the portable terminals 120. The first transmitter/receiver 44 is configured or programmed such that if the information on the surgical instrument set 80 is updated by the changer 46, the first transmitter/receiver 44 transmits the updated information on the surgical instrument set 80 to the portable terminals 120. Upon receiving information on the identification unit 84 transmitted from the information acquisition device 85 (see FIG. 10), the first transmitter/receiver 44 transmits, to the portable terminals 120, information on the surgical instrument set 80 associated with the identification unit 84. Thus, updated information on the surgical instrument set 80 stored in the memory 42 is transmitted to the portable terminals 120.

The information changer 46 updates information on the surgical instrument set 80 stored in the memory 42. More specifically, the changer 46 is configured or programmed such that when the changed information on the surgical instrument set 80 is transmitted from the second transmitter/receivers 124 (see FIG. 14) of the portable terminals 120 to the server 40, that is, when the first transmitter/receiver 44 receives the changed information on the surgical instrument set 80 transmitted from the second transmitter/receiver 124, the changer 46 updates information on the surgical instrument set 80 stored in the memory 42 to the changed information on the surgical instrument set 80.

The operator information acquirer 48 acquires information on an operator that performs the steps of the circulation cycle 70 (see FIG. 11). Here, to use the surgical instrument set management system 110 according to this preferred embodiment, it is necessary to acquire an account with which predetermined information is registered. The account is assigned personal information or the like, and an operator is able to be identified by the account. Each account is assigned an ID and a password. The operator inputs an ID and a password to log in the surgical instrument set management system 110 with this account. When the operator logs in the surgical instrument set management system 110, the operator information acquirer 48 acquires information on the operator (e.g., the name of the account, date of log-in, etc.). The acquired information on the operator is stored in the memory 42.

When a change of information on the surgical instrument set 80 is input by the operator, the change recorder 50 records information on the operator who input the change. As the information on the operator, the change recorder 50 records the account name of the operator, the date of the change, and so forth. The change recorder 50 associates information on the surgical instrument set 80 with information on the operator who input the change. The recorded information on the operator is stored in the memory 42. When the first transmitter/receiver 44 receives information on the changed surgical instrument set 80 transmitted from the second transmitter/receiver 124, the change recorder 50 records information on the operator.

Figure 13:
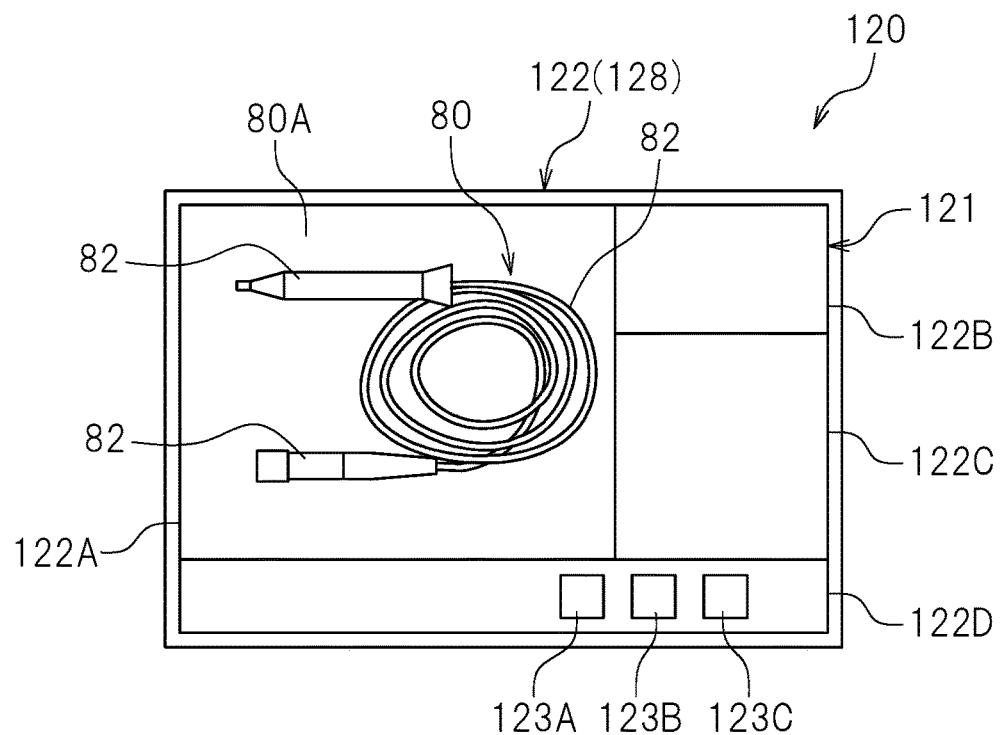
FIG. 13 is a schematic view of a portable terminal according to a preferred embodiment of the present invention.
Figure 14:
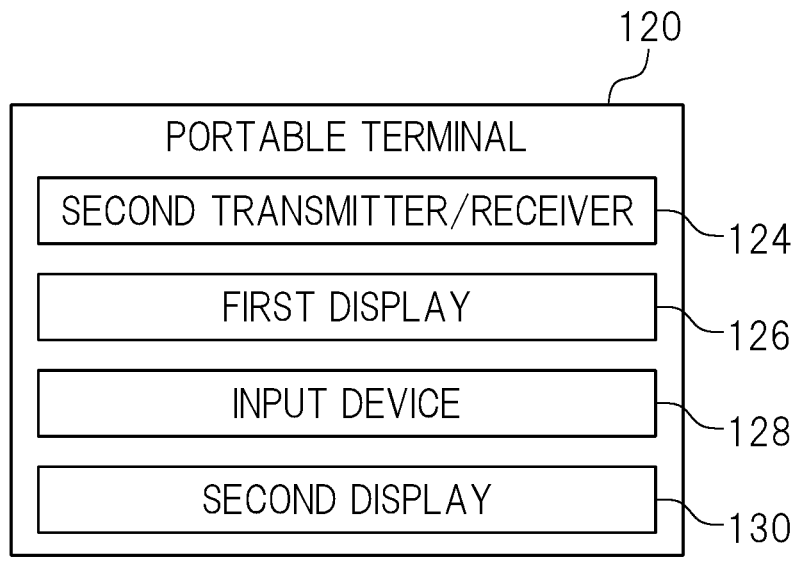
FIG. 14 is a block diagram illustrating a configuration of a portable terminal according to a preferred embodiment of the present invention.

As illustrated in FIGS. 13 and 14, each of the portable terminals 120 includes a display screen 122, a second transmitter/receiver 124, a first display 126, an input device 128, and a second display 130. As illustrated in FIG. 13, the display screen 122 displays information on the surgical instrument set 80.

The second transmitter/receiver 124 transmits and receives information on the surgical instrument set 80 to/from the server 40. More specifically, the second transmitter/receiver 124 transmits and receives information on the surgical instrument set 80 transmitted from the first transmitter/receiver 44. The second transmitter/receiver 124 transmits information on the changed surgical instrument set 80 to the server 40. If the information on the surgical instrument set 80 is changed by the input device 128, the second transmitter/receiver 124 transmits the information on the changed surgical instrument set 80 to the first transmitter/receiver 44.

Figure 15:
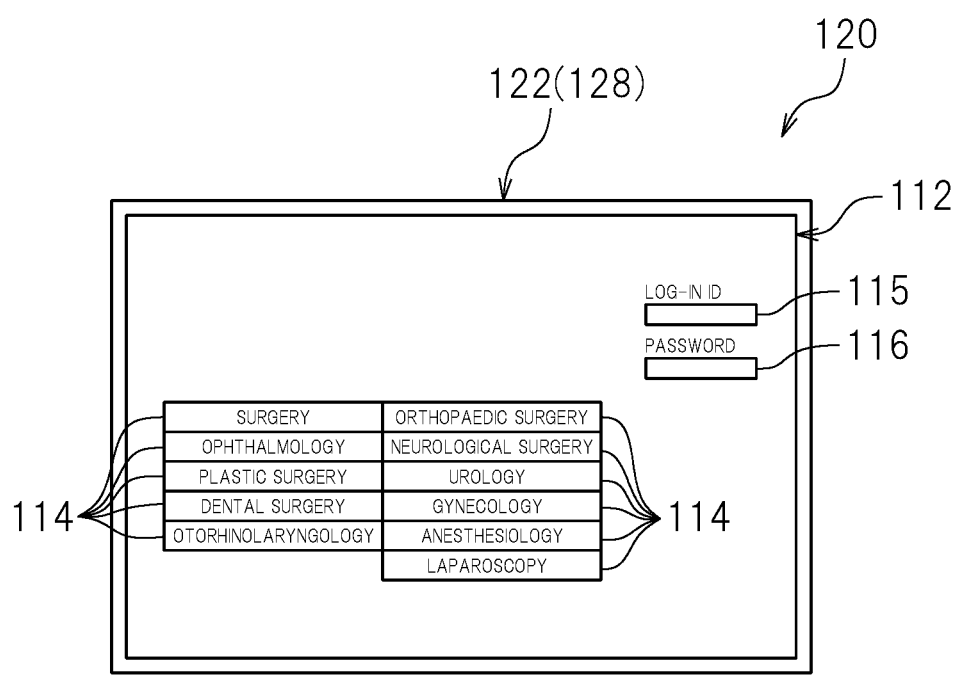
FIG. 15 is a view illustrating a state where a search screen is displayed on a display screen according to a preferred embodiment of the present invention.
Figure 16:
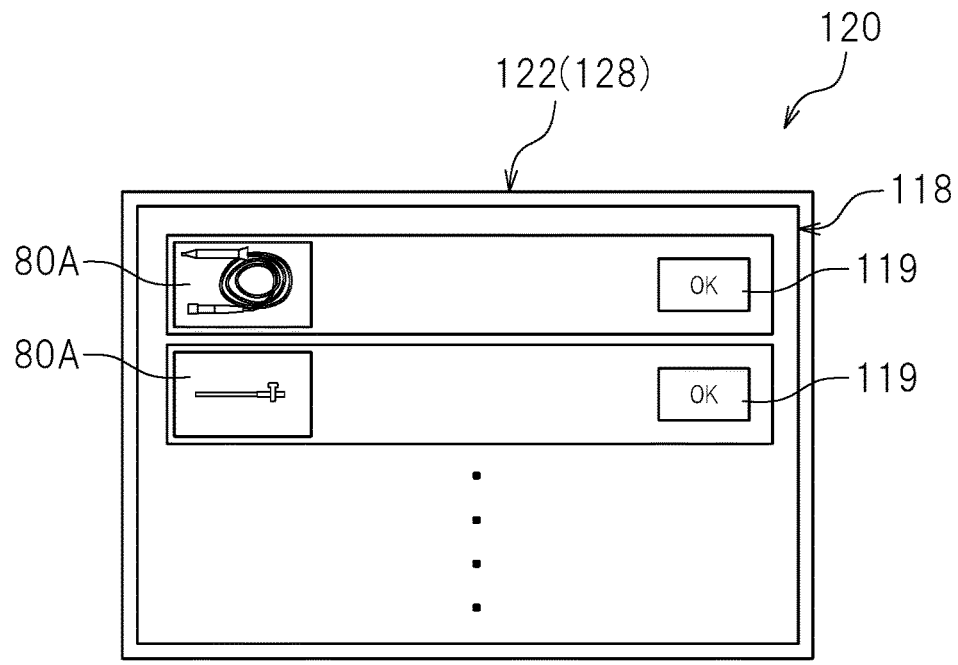
FIG. 16 is a view illustrating a state where a list screen is displayed on a display screen according to a preferred embodiment of the present invention.

The first display 126 causes the display screen 122 to display a search screen 112 (see FIG. 15) and a list screen 118 (see FIG. 16). As illustrated in FIG. 15, the display screen 122 of the portable terminal 120 displays the search screen 112. The search screen 112 is provided with a plurality of virtual buttons 114 to select hospital departments, an ID region 115 to which an ID of an account is input, and a password region 116 to which a password is input. As illustrated in FIG. 16, the display screen 122 of the portable terminal 120 displays the list screen 118. The list screen 118 displays a plurality of photographs 80A of previously recorded surgical instrument sets 80 and buttons 119 to select the surgical instrument sets 80 including the photographs 80A. When one of the buttons 119 is pressed, the first transmitter/receiver 44 transmits information on the surgical instrument set 80 associated with the buttons 119 to the portable terminal 120.

As illustrated in FIG. 13, the first display 126 causes the display screen 122 to display the information display screen 121. The information display screen 121 displays information on the surgical instrument set 80 received by the second transmitter/receiver 124. The information display screen 121 includes a first region 122A to display the photograph 80A of the surgical instrument set 80, a second region 122B to display basic information of the surgical instrument set 80, a third region 122C to display a memo field, and a fourth region 122D to display virtual buttons 123A, 123B, and 123C for the input device 128. Here, the fourth region 122D displays a photograph button 123A, an item button 123B, and a memo button 123C, for example. The photograph button 123A receives an operation concerning a change of the photographs 80A of the surgical instrument sets 80, and is used to change the photographs 80A. The item button 123B receives an operation concerning a change of basic information on the surgical instrument sets 80, and is used to change basic information. The memo button 123C receives an operation concerning a memo of the surgical instrument sets 80, and is used to write a memo.

Figure 17:
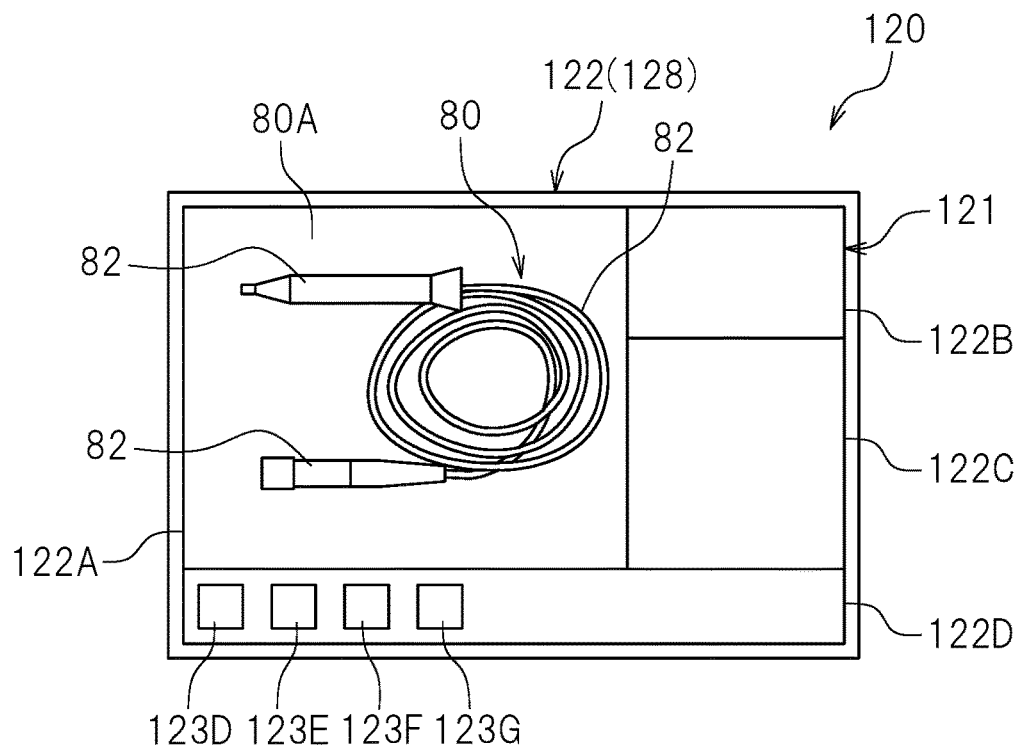
FIG. 17 is a view illustrating a state where an editing tool is displayed on a display screen according to a preferred embodiment of the present invention.

When the memo button 123C is operated through the input device 128, as illustrated in FIG. 17, the first display 126 displays editing tool buttons for use in editing information on the surgical instrument set 80 on the fourth region 122D of the information display screen 121. Here, the first display 126 displays virtual buttons for the input device 128, such as a color change button 123D, a figure button 123E, a delete button 123F, and a register button 123G, on the fourth region 122D. The color change button 123D is used to change colors of a text or a figure in a memo. The figure button 123E is used to specify a figure in taking a memo. The delete button 123F is used to delete a memo. The register button 123G is used to register a text or a figure in taking a memo.

To the input device 128, a change of information on the surgical instrument sets 80 is input by an operator. In this preferred embodiment, the input device 128 is a touch panel disposed on the surface of the display screen 122. The input device 128 may be a mouse, a keyboard, or the like. In this preferred embodiment, through the input device 128, the operator can operate various buttons displayed on the display screen 122 (i.e., the search screen 112, the list screen 118, and the information display screen 121). In addition, through the input device 128, a handwritten memo can be added to information displayed on the information display screen 121 of the display screen 122. The handwritten memo is added with, for example, a touch pen.

Figure 18:
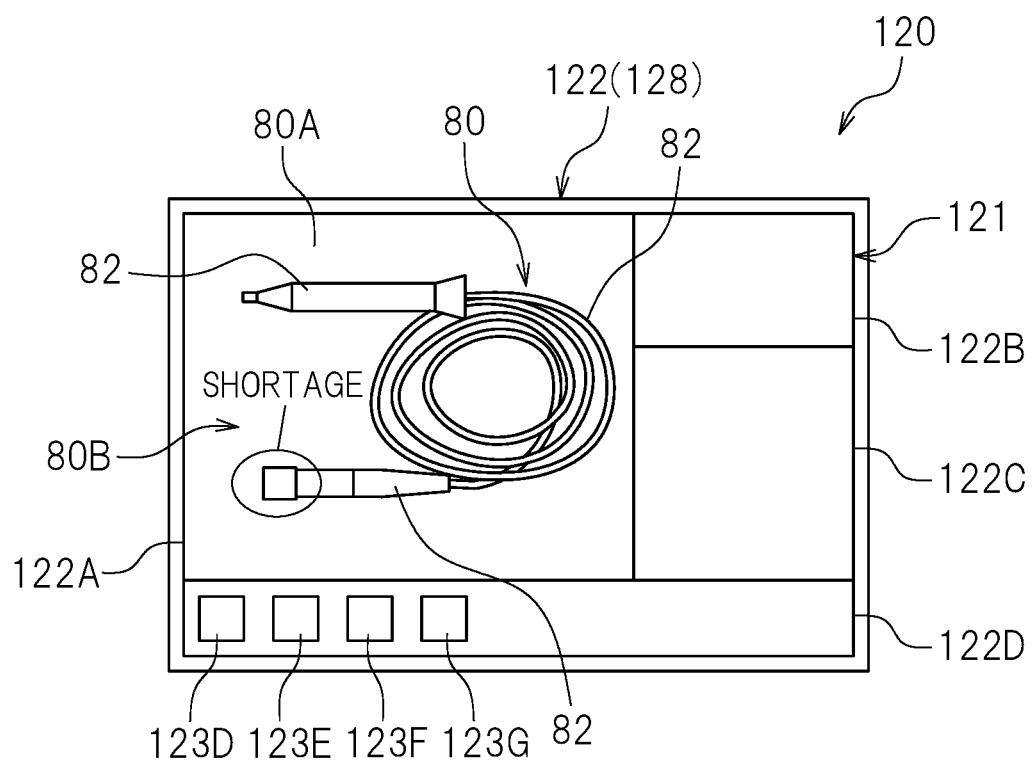
FIG. 18 is a view illustrating a state where a memo is displayed on a display screen according to a preferred embodiment of the present invention.

The second display 130 causes the information display screen 121 to display information on the changed surgical instrument set 80. For example, as illustrated in FIG. 18, the second display 130 displays a memo 80B added by the input device 128 on the information display screen 121. Here, when the register button 123G is operated, details of this operation (i.e., information on the changed surgical instrument set 80) are transmitted by the second transmitter/receiver 124 to the server 40. Each of the first display 126 and the second display 130 can be implemented by, for example, a central processing unit (CPU) or a read only memory (ROM) or a RAM (random access memory) storing programs or the like to be executed by the CPU.

Next, a procedure in which an operator changes information on the surgical instrument sets 80 with the surgical instrument set management system 110 will be described. Here, a change of information on the surgical instrument sets 80 will be described for a case in the assembly step 74 of the circulation cycle 70, as an example. As illustrated in FIG. 15, the display screen 122 of the portable terminal 120 displays the search screen 112. First, the operator inputs an ID of an account to the ID region 115, and inputs a password to the password region 116. Accordingly, the operator can log in the surgical instrument set management system 110. Next, the operator operates the input device 128 to press one of the buttons 114 to select a surgery department on the search screen 112. Accordingly, as illustrated in FIG. 16, the display screen 122 displays the list screen 118. The operator operates the input device 128 to press one of the buttons 119 associated with a surgical instrument set 80 the operator wants to check. Accordingly, information on the surgical instrument set 80 is transmitted from the first transmitter/receiver 44 of the server 40 to the portable terminal 120, and as illustrated in FIG. 13, the display screen 122 displays the information display screen 121 on which information on the surgical instrument set 80 is displayed. Here, in a case where information on the surgical instrument set 80 needs to be changed, the surgical instrument set management system 110 according to this preferred embodiment enables the operator to directly input details of the change to the information display screen 121. The operator operates the input device 128 to press the memo button 123C. Accordingly, as illustrated in FIG. 18, the operator can add the memo 80B to the photograph 80A displayed on the information display screen 121. Thereafter, the operator presses the register button 123G so that the second transmitter/receiver 124 transmits the information on changed the surgical instrument set 80 (i.e., information in which the memo 80B is added to the information on the surgical instrument set 80) to the server 40. Accordingly, the changer 46 of the server 40 updates information on the surgical instrument set 80 stored in the memory 42 to the information on the changed surgical instrument set 80. Subsequently, when the operator views the information on the surgical instrument set 80 described above, the first transmitter/receiver 44 of the server 40 transmits the updated information on the surgical instrument set 80 to the portable terminals 120, and thus, the operator is able to check the updated information on the surgical instrument set 80.

As described above, in the surgical instrument set management system 110 according to this preferred embodiment, in the case where the operator changes information on the surgical instrument set 80 through the input device 128, the second transmitter/receiver 124 of the portable terminal 120 transmits the information on the changed surgical instrument set 80 to the server 40. Accordingly, in the changer 46 of the server 40, information on the surgical instrument set 80 is updated to the latest information. Then, if the information on the surgical instrument set 80 is updated, the first transmitter/receiver 44 of the server 40 transmits the updated information on the surgical instrument set 80 to the portable terminal 120. Accordingly, every time the operator using the portable terminal 120 checks information on the surgical instrument set 80, the operator is able to acquire information on the surgical instrument set 80 on which the latest change is reflected. In this manner, when information on the surgical instrument set 80 is changed in one of the portable terminals 120, the updated information is transmitted to the server 40, and the information on the surgical instrument set 80 is updated in the server 40. Thus, information on the surgical instrument set 80 is able to be easily managed. When the operator checks information on a specific surgical instrument set using the portable terminal 120, since the information is updated to the latest information, the operator is able to know details of a change in a work accurately and promptly so that a failure in communication is prevented.

In the preferred embodiment described above, the number of portable terminals 120 connected to the server 40 is four, for example. The present invention, however, is not limited to this example. Two or three or five or more portable terminals 120 may be provided.

In surgery in a hospital, a plurality of surgical instrument sets each including a plurality of surgical instruments have been conventionally used to date. In a hospital, each surgical instrument set circulates in a circulation cycle including the following steps.

Specifically, the circulation cycle includes: a surgery step of performing surgery on a patient with a stored surgical instrument set; a collection step of collecting the surgical instrument set used for the surgery; a cleaning step of cleaning the collected surgical instrument set; an assembly step of assembling the cleaned surgical instrument set; a sterilization step of sterilizing the assembled surgical instrument set; and a storage step of storing the sterilized surgical instrument set. To assemble the surgical instrument set refers to returning surgical instruments individually cleaned in the cleaning step to a predetermined surgical instrument set.

Here, surgical instrument sets differ among types of surgery and doctors using the surgical instrument sets, and there is a wide variety of surgical instrument sets. In addition, the number of surgical instruments included in one surgical instrument set significantly varies.

In a hospital, urgent surgery is also performed in addition to general surgery. Thus, if works in the steps in the circulation cycle can be completed quickly, urgent surgery can be more quickly started.

Here, if a surgical instrument included in the surgical instrument set is broken in the steps, the broken surgical instrument is delivered to be repaired or an order for a new surgical instrument is issued in some cases. Surgical instruments can be lent to another surgical instrument set in some cases. That is, a surgical instrument set can be missing some of surgical instruments in some cases. Even in a case where a change is made for a surgical instrument set, such as a shortage of a surgical instrument, some types of surgery can be performed without problems. Thus, in hospitals, even if a change such as a shortage is present for a surgical instrument set, a work needs to be completed before the storage step of storing a surgical instrument set in preparation for surgery. At this time, it is required that details of a surgical instrument set are always stored in a state updated to the latest information. Accordingly, it is supposed that if an operator at each step can correctly and quickly know a change in a surgical instrument set, a work time at each step is able to be reduced, and the time necessary for one circulation cycle is able to be reduced.

In view of this, additional preferred embodiments of the present invention provide a surgical instrument set management system that easily manages a change in a surgical instrument set and transmits details of the change to persons concerned correctly and quickly.

A preferred embodiment of the present invention provides a surgical instrument set management system. The surgical instrument set management system is a surgical instrument set management system that manages a change in a surgical instrument set including a plurality of surgical instruments in a surgery cycle including a surgery step, a collection step, a cleaning step, an assembly step, a sterilization step, and a storage step, and includes a server, and a plurality of portable terminals each of which can communicate with the server and has a display screen. The server includes a memory that stores information on a surgical instrument set including a plurality of surgical instruments, a first transmitter/receiver that receives and transmits information on the surgical instrument set, and a changer that updates the information on the surgical instrument set. Each of the portable terminals includes a second transmitter/receiver that transmits and receives the information on the surgical instrument set to/from the server, a first display that causes the display screen to display the received information on the surgical instrument set, an input device to which a change of the information on the surgical instrument set is input by an operator, and a second display that causes the display screen to display the information on the changed surgical instrument set. The second transmitter/receiver transmits the information on the changed surgical instrument set to the server. The changer is configured or programmed such that when the information on the changed surgical instrument set is transmitted from the second transmitter/receiver to the server, the changer updates the information on the surgical instrument set. The first transmitter/receiver is configured or programmed such that when the information on the surgical instrument set is updated, the first transmitter/receiver transmits the updated information on the surgical instrument set to the portable terminal.

In this configuration, when an operator changes information on the surgical instrument set through the input device, the second transmitter/receiver of the portable terminal transmits the information on the changed surgical instrument set. Accordingly, the changer of the server updates the information on the surgical instrument set to the latest information. Then, if the information on the surgical instrument set is updated, the first transmitter/receiver of the server transmits the updated information on the surgical instrument set to at least one of the portable terminals. Accordingly, every time the operator using the portable terminal checks information on the surgical instrument set, the operator is able to acquire information on the surgical instrument set on which the latest change is reflected. In this manner, when information on the surgical instrument set is changed in one of the portable terminals, the updated information is transmitted to the server, and the information on the surgical instrument set is updated in the server. Thus, information on the surgical instrument set is able to be easily managed. When the operator checks information on a specific surgical instrument set using the portable terminal, since the information is updated to the latest information, the operator is able to know details of a change in a work accurately and promptly.

In a first preferred embodiment of the first aspect, each of the surgical instruments of the surgical instrument set includes an identification unit assigned information on the surgical instrument set, the surgical instrument set management system also includes an information acquisition device that transmits the information on the identification unit to the server, and when the first transmitter/receiver of the server receives the information on the identification unit transmitted from the information acquisition device, the first transmitter/receiver transmits information on the surgical instrument set associated with the identification unit to the portable terminal.

In this preferred embodiment, the information associated with the surgical instrument set is displayed on the display screen only by acquiring information on the identification unit of one of the surgical instruments of the surgical instrument set. Thus, acquisition of information on the surgical instrument set and a confirmation of a change is able to be easily performed.

In another preferred embodiment of the first aspect, the server includes an operator information acquirer that acquires information on an operator, and a change recorder that, when an operator inputs a change of information on the surgical instrument set, records information on the operator who input the change.

In this preferred embodiment, it is clear which operator changed information on the surgical instrument set. Accordingly, even if details of the change are unclear, the operator can be specified. Thus, a modification of the change is able to be easily performed.

In another preferred embodiment of the present invention, the input device is a touch panel disposed on the display screen.

In this preferred embodiment, the operator is able to easily change the information on the surgical instrument set by directly touching the display screen.

In another preferred embodiment of the present invention, the information on the surgical instrument set includes a photograph indicating the surgical instrument set, and the operator inputs a change of the information on the surgical instrument set to the photograph with the input device.

In this preferred embodiment, a place of the change in the surgical instrument set is able to be more easily checked.

Fourth Preferred Embodiment

Next, a surgical instrument set management system according to another preferred embodiment of the present invention will be described. The surgical instrument set management system according to this preferred embodiment manages a surgical instrument set in which icons indicating details of a work to be checked are previously associated with information on a surgical instrument set including a plurality of surgical instruments. The "icon" herein refers to a figure or a pictogram that is a simplified symbol indicating an instruction, a command, or the like given to a computer.

Figure 19:
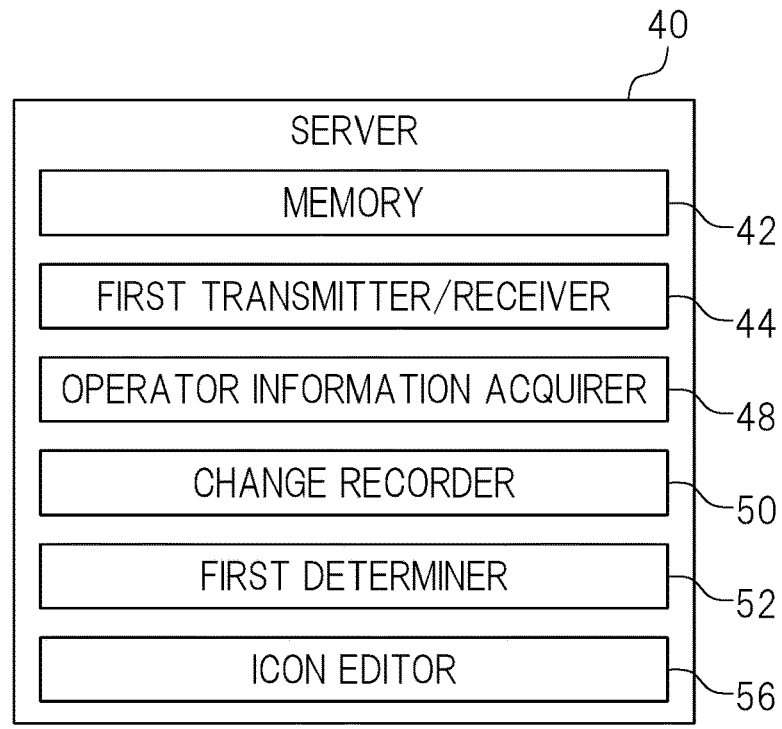
FIG. 19 is a block diagram illustrating a configuration of a server according to another preferred embodiment of the present invention.

As illustrated in FIG. 19, the server 40 includes a memory 42, a first transmitter/receiver 44, an operator information acquirer 48, a change recorder 50, a first determiner 52, and an icon editor 56.

Figure 20:
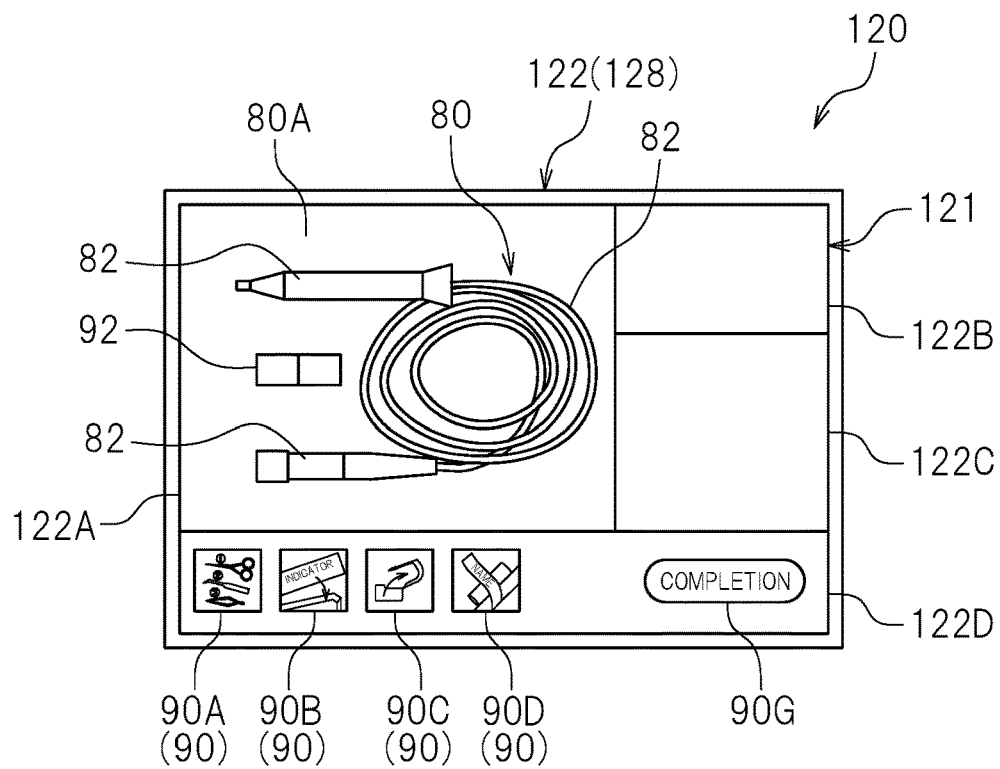
FIG. 20 is a schematic view of a portable terminal according to another preferred embodiment of the present invention.

The memory 42 stores icons 90 indicating details of works to be checked (see FIG. 20). The memory 42 stores association between information on the surgical instrument set 80 and the icons 90. The icons 90 and the information on the surgical instrument set 80 are previously stored in the memory 42.

The icons 90 are represented as patterns for easy understanding of details of works at a glance. As illustrated in FIG. 20, the icons 90 include, for example, a number check icon 90A, an indicator check icon 90B, a name input icon 90C, and a sealing member attachment icon 90D. The number check icon 90A indicates a work of checking the number of surgical instruments 82 (see FIG. 10) included in the surgical instrument set 80 (see FIG. 10). The indicator check icon 90B indicates a work of determining whether an indicator 92 (see FIG. 20) is enclosed in the surgical instrument set 80. Here, the indicator 92 refers to an indicator that changes in color with sufficient sterilization and does not change in color with insufficient sterilization, and is used to determine whether sterilization is carried out or not. The name input icon 90C indicates a work of housing the surgical instrument set 80 in a predetermined case, attaching a sterilization tape to an opening/closing portion of the case, and writing the name of an operator on the sterilization tape. The sterilization tape herein refers to a tape including a surface on which a pattern is formed when sterilization is performed, and is used to determine whether sterilization is performed or not. The sealing member attachment icon 90D indicates a work of attaching a sealing member of inhibiting opening and closing of the case to the case. The sealing member herein refers to a sealing wire, a sealing seal, or the like that inhibits opening and closing of the case, and proves that the case is neither opened nor closed unless the sealing member is broken. The memory 42 can store a newly added icon 90 at any time.

The first transmitter/receiver 44 transmits and receives information on the surgical instrument set 80 and icons 90 associated with the information on the surgical instrument set 80 (hereinafter referred to as "icon-assigned surgical instrument set information"). More specifically, the first transmitter/receiver 44 transmits the icon-assigned surgical instrument set information to each of the portable terminals 120. The first transmitter/receiver 44 receives work completion information from the portable terminals 120. When the first transmitter/receiver 44 receives information on the identification unit 84 from the information acquisition device 85 (see FIG. 10), the first transmitter/receiver 44 transmits icon-assigned surgical instrument set information associated with the identification unit to the portable terminal 120. If the first determiner 52 determines that operators are identical as described later, the first transmitter/receiver 44 does not transmit the icon-assigned surgical instrument set information to the portable terminal 120.

When an operator inputs a confirmation of work details displayed on the icons 90 through the input device 128 of the portable terminal 120 (see FIG. 20) as described later, the change recorder 50 records information on the operator who input the confirmation. The change recorder 50 records, as information on the operator, the name of an account of the operator and date of the confirmation, and so forth. The recorded information on the operator is stored in the memory 42. When the first transmitter/receiver 44 receives work completion information from the second transmitter/receiver 124, for example, the change recorder 50 records information on the operator.

The first determiner 52 determines whether an operator performing a current step is identical to an operator who performed the immediately preceding step or not. For example, in a case where the current step is the sterilization step 75 (see FIG. 11) and the immediately preceding step is the assembly step 74 (see FIG. 11), the first determiner 52 determines whether operators are identical or not by comparing account information of an operator who is to perform the sterilization step 75 with account information of an operator who performed the assembly step 74.

The icon editor 56 edits the icons 90 associated with the surgical instrument set 80. To "edit an icon 90" includes addition of an icon 90 and deletion of an icon 90.

Figure 21:
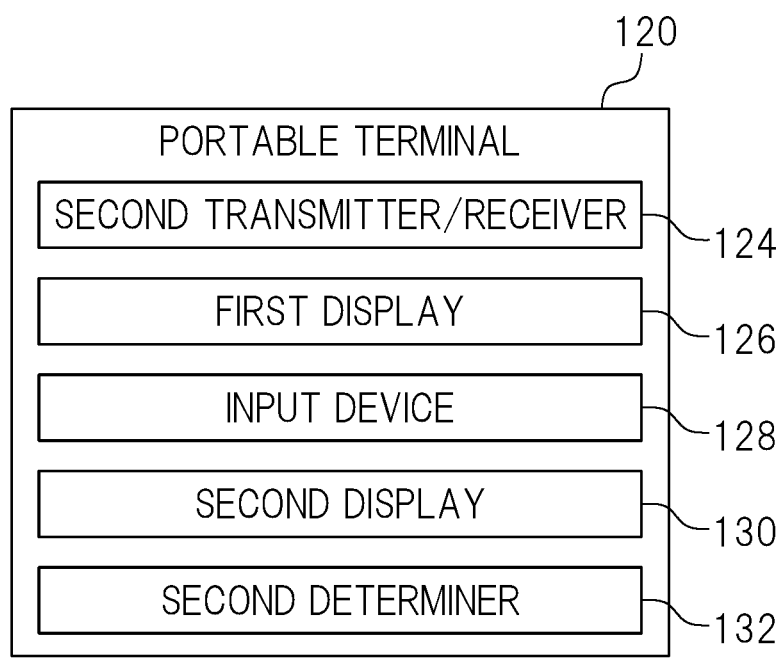
FIG. 21 is a block diagram illustrating a configuration of a portable terminal according to another preferred embodiment of the present invention.

As illustrated in FIGS. 20 and 21, each of the portable terminals 120 includes a display screen 122, a second transmitter/receiver 124, a first display 126, an input device 128, a second display 130, and a second determiner 132. As illustrated in FIG. 20, the display screen 122 displays icon-assigned surgical instrument set information.

The second transmitter/receiver 124 transmits and receives icon-assigned surgical instrument set information to/from the server 40 (see FIG. 10). More specifically, the second transmitter/receiver 124 receives icon-assigned surgical instrument set information transmitted from the first transmitter/receiver 44 (see FIG. 19). If a confirmation of work details indicated by all the icons 90 is input with the input device 128, the second transmitter/receiver 124 transmits work completion information to the first transmitter/receiver 44 of the server 40.

Figure 22:
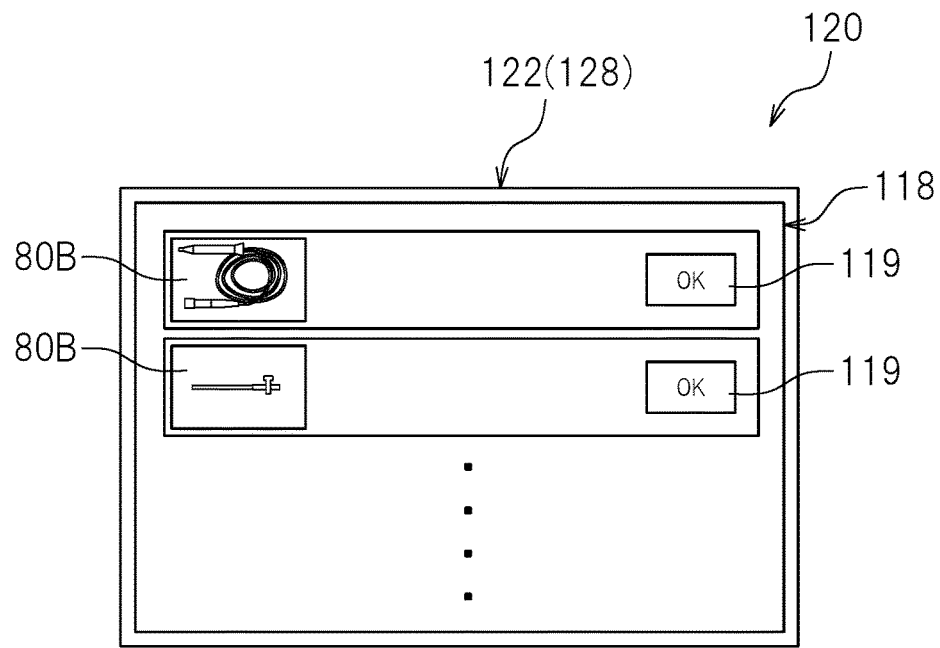
FIG. 22 is a view illustrating a state where a list screen is displayed on a display screen according to another preferred embodiment of the present invention.

As illustrated in FIG. 22, the list screen 118 displays photographs 80B of a plurality of surgical instrument sets 80 for which a work at the immediately preceding step is completed, and buttons 119 to select surgical instrument sets 80 including the photographs 80B. That is, at a step, if a work at the immediately preceding step is not completed, photographs 80B of surgical instrument sets 80 for which a work is not completed, for example, are not displayed on the list screen 118. When one of the buttons 119 is pressed, the first transmitter/receiver 44 transmits icon-assigned surgical instrument set information of the surgical instrument set 80 associated with this button 119 to the portable terminals 120.

As illustrated in FIG. 20, the first display 126 causes the display screen 122 to display the information display screen 121. The information display screen 121 displays icon-assigned surgical instrument set information received by the second transmitter/receiver 124. The information display screen 121 includes a first region 122A to display the photograph 80B of the surgical instrument set 80, a second region 122B to display basic information of the surgical instrument set 80, a third region 122C to display a memo field, and a fourth region 122D to display the icons 90. Here, for example, the fourth region 122D displays the number check icon 90A, the indicator check icon 90B, the name input icon 90C, and the sealing member attachment icon 90D. The icons 90 displayed on the fourth region 122D are buttons for use in switching a check mark 95 (see FIG. 23) between display and non-display. The first display 126 causes the information display screen 121 to display a completion button 90G that is a button used when all the check works are completed.

If the first determiner 52 of the server 40 determines that an operator performing a current step is identical to an operator who performed the immediately preceding step, the first display 126 causes the information display screen 121 not to display icon-assigned surgical instrument set information. More specifically, if the first determiner 52 determines that the operators are identical, the first transmitter/receiver 44 of the server 40 does not transmit the icon-assigned surgical instrument set information to the portable terminals 120, and thus, the first display 126 cannot display the icon-assigned surgical instrument set information on the information display screen 121.

Figure 24:
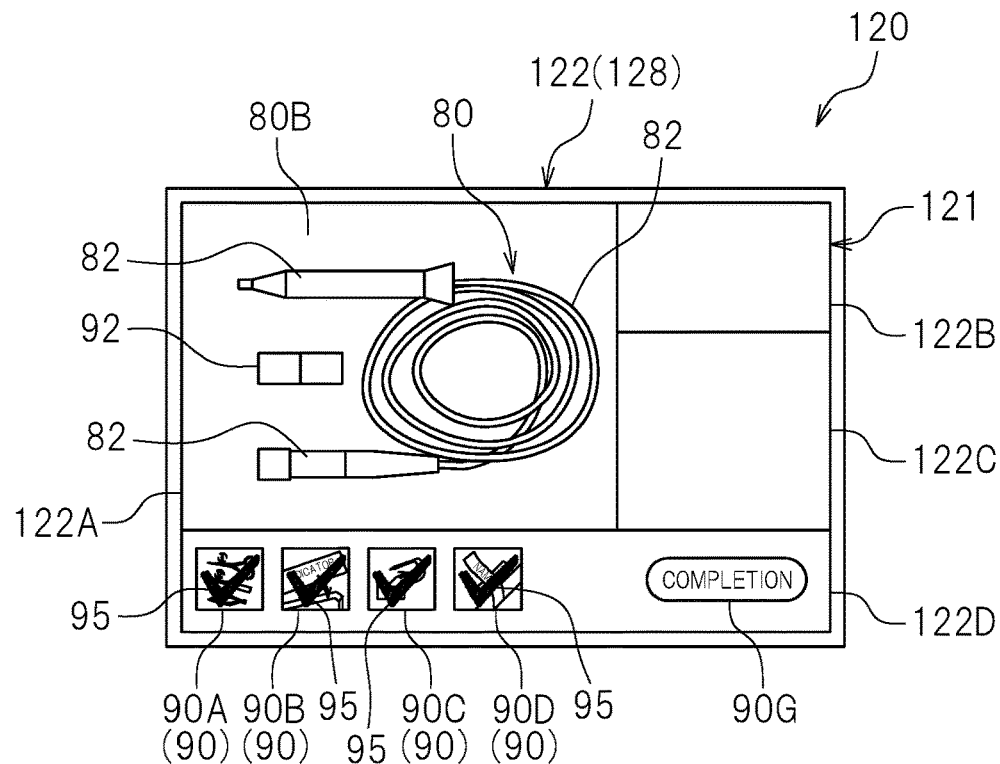
FIG. 24 is a view illustrating a state where an information display screen is displayed on a display screen according to a preferred embodiment of the present invention.

To the input device 128, an operator inputs a confirmation of work details indicated by icons 90. In this preferred embodiment, the input device 128 is a touch panel disposed on the surface of the display screen 122. The input device 128 may be a mouse, for example. In this preferred embodiment, through the input device 128, the operator is able to operate various buttons displayed on the display screen 122 (i.e., the search screen 112, the list screen 118, and the information display screen 121). The input device 128 is configured such that if the second determiner 132 determines that a confirmation of all the icons 90 has been input as described later, the input device 128 accepts an input of completion of all the details of works by an operator. That is, as illustrated in FIG. 24, when a confirmation of all the icons 90 is input (i.e., check marks 95 are displayed for all the icons 90), the operator operates the completion button 90G through the input device 128 to complete a check work.

Figure 23:
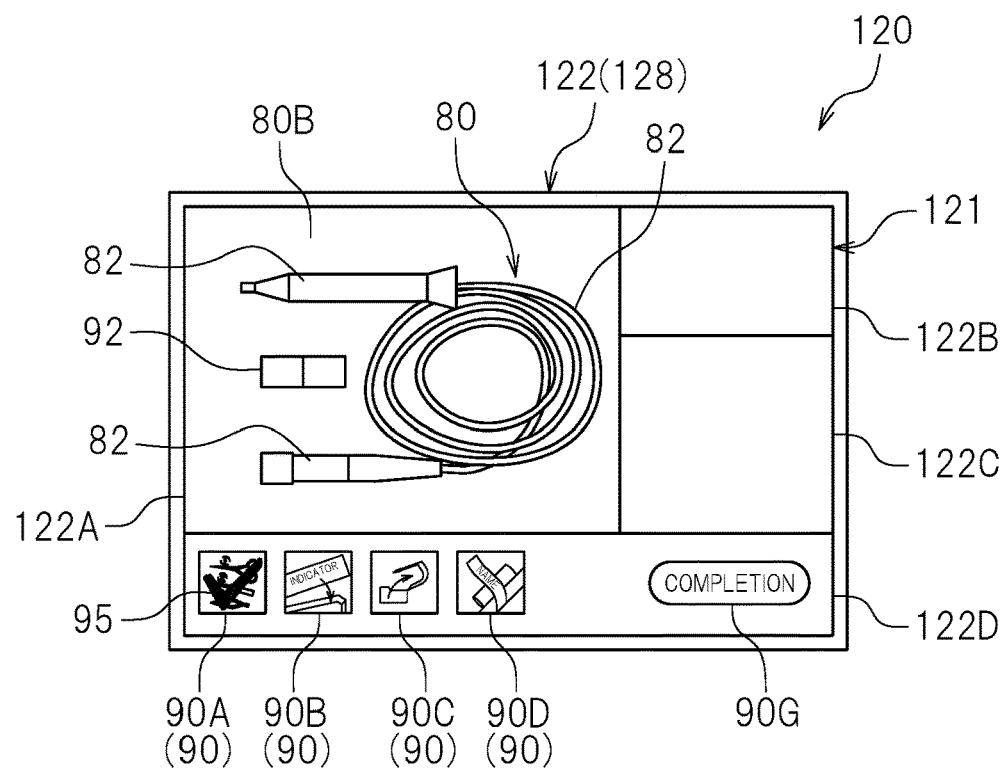
FIG. 23 is a view illustrating a state where an information display screen is displayed on the display screen according to a preferred embodiment of the present invention.
Figure 25:
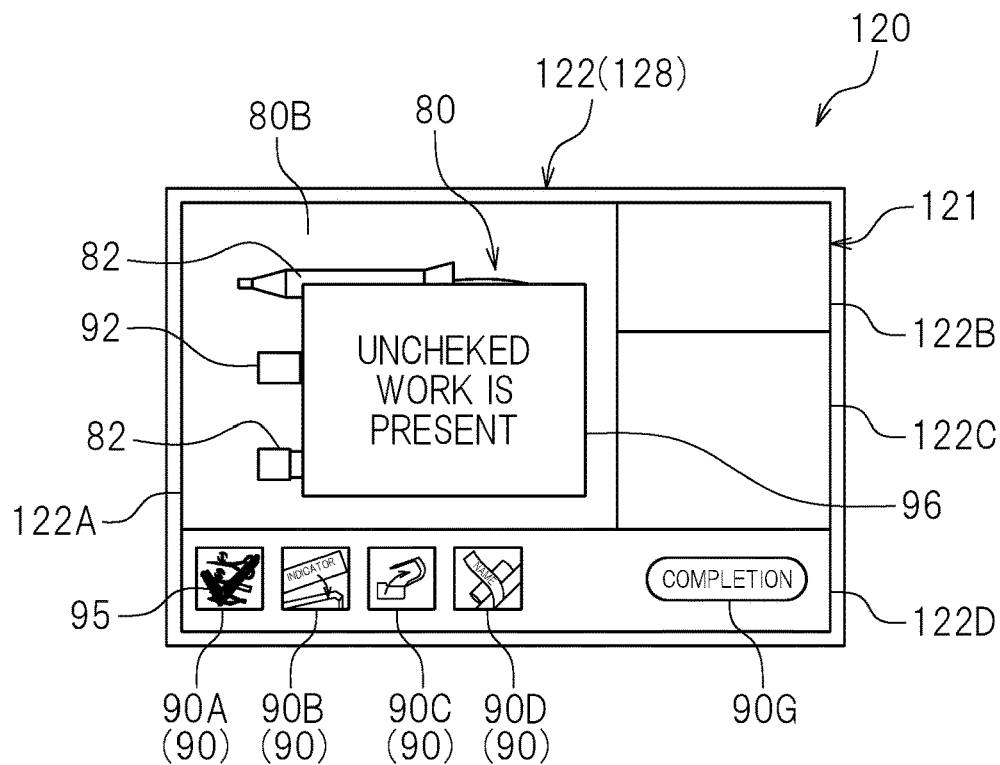
FIG. 25 is a view illustrating a state where an information display screen is displayed on a display screen according to a preferred embodiment of the present invention.

The second display 130 causes the information display screen 121 to display details input through the input device 128 with respect to icons 90. That is, as illustrated in FIG. 23, the second display 130 displays the check marks 95 on the icons 90. That is, when an icon 90 is operated through the input device 128, the second display 130 displays a check mark 95 on the icon 90, and when the icon 90 is operated with the check mark 95 displayed on the icon 90, another icon 90 provided with no check mark 95 is displayed. As illustrated in FIG. 25, the second display 130 notifies an operator that a check work is not completed for all the icons 90. For example, when an operator operates the completion button 90G in a state where check marks 95 are not displayed on all the icons 90 (see FIG. 23), the second display 130 displays a warning screen 96 on the information display screen 121, as illustrated in FIG. 25.

The second determiner 132 determines whether a confirmation with the input device 128 is input for all the icons 90 associated with the surgical instrument set 80 or not. The second determiner 132 determines whether check marks 95 are displayed on all the icons 90 displayed on the information display screen 121, for example. At this time, when one of the icons 90 is operated through the input device 128, for example, a signal indicating that a check mark 95 is displayed on the icon 90 is transmitted to the second determiner 132.

Next, a procedure in which an operator checks details of a work associated with the surgical instrument set 80 with the surgical instrument set management system 110 will be described. Here, checking of details of a work associated with the surgical instrument set 80 will be described using a case in the sterilization step 75 of the circulation cycle 70 as an example. As illustrated in FIG. 15, the display screen 122 of the portable terminal 120 displays the search screen 112. First, the operator inputs an ID of an account to the ID region 115, and inputs a password to the password region 116. Accordingly, the operator is able to log in the surgical instrument set management system 110. Next, the operator operates the input device 128 to press one of the buttons 114 to select a surgery department on the search screen 112. Accordingly, as illustrated in FIG. 22, the display screen 122 displays a list screen 118. If it is determined that an operator in the assembly step 74 is identical to an operator in the sterilization step 75, information on the surgical instrument set 80 used by the identical operator in the assembly step 74 is not displayed on the list screen 118. That is, the list screen 118 displays only the surgical instrument set 80 used by an operator different from an operator at a current step (the sterilization step 75 in this example) in the immediately preceding step (the assembly step 74 in this example). The operator operates the input device 128 to press one of the buttons 119 associated with a surgical instrument set 80 the operator wants to check. Accordingly, icon-assigned surgical instrument set information is transmitted from the first transmitter/receiver 44 of the server 40 to the portable terminals 120, and as illustrated in FIG. 20, the display screen 122 displays information on the surgical instrument set 80 and the information display screen 121 displaying the icons 90A through 90D associated with the surgical instrument set 80. In this manner, since the check work in the sterilization step 75 is displayed by the icons 90A through 90D, the operator is able to promptly understand what the operator should check in the sterilization step 75. When the operator checks details of works associated with the icons 90A through 90D, the operator operates the input device 128 and presses the icons 90A through 90D. Then, the operator presses the completion button 90G with the check marks 95 displayed on the icons 90A through 90D. Accordingly, the second transmitter/receiver 44 transmits work completion information to the first transmitter/receiver 44 of the server 40. Thereafter, information on the surgical instrument set 80 is updated, and the process then proceeds to the next storage step 76.

In the manner described above, in the surgical instrument set management system 110 according to this preferred embodiment, details of works in the steps of the circulation cycle 70 are represented by icons and the icons 90 are displayed on the display screen 122. Thus, even a beginner operator can easily understand details of works. In addition, since details of works represented by icons are associated with the surgical instrument sets 80 beforehand, it is possible to prevent details of works in the steps from varying among operators. Furthermore, since check results of details of works are displayed on the display screen 122, missing of checking for details of works is reduced or prevent, and progress statuses of other operators are able to be checked. In a case where the first determiner 52 of the server 40 determines that an operator performing a current step is identical to an operator who performed the immediately preceding step, the first display 126 of the portable terminal 120 does not cause the display screen 122 to display information on the surgical instrument set 80 and the icons 90 associated with the information on the surgical instrument set 80. Accordingly, it becomes necessary to make an operator performing a current step different from an operator who performed the immediately preceding step, and thus, double checking by different operators is able to be performed. As a result, quality of the check work is enhanced.

Figure 26:
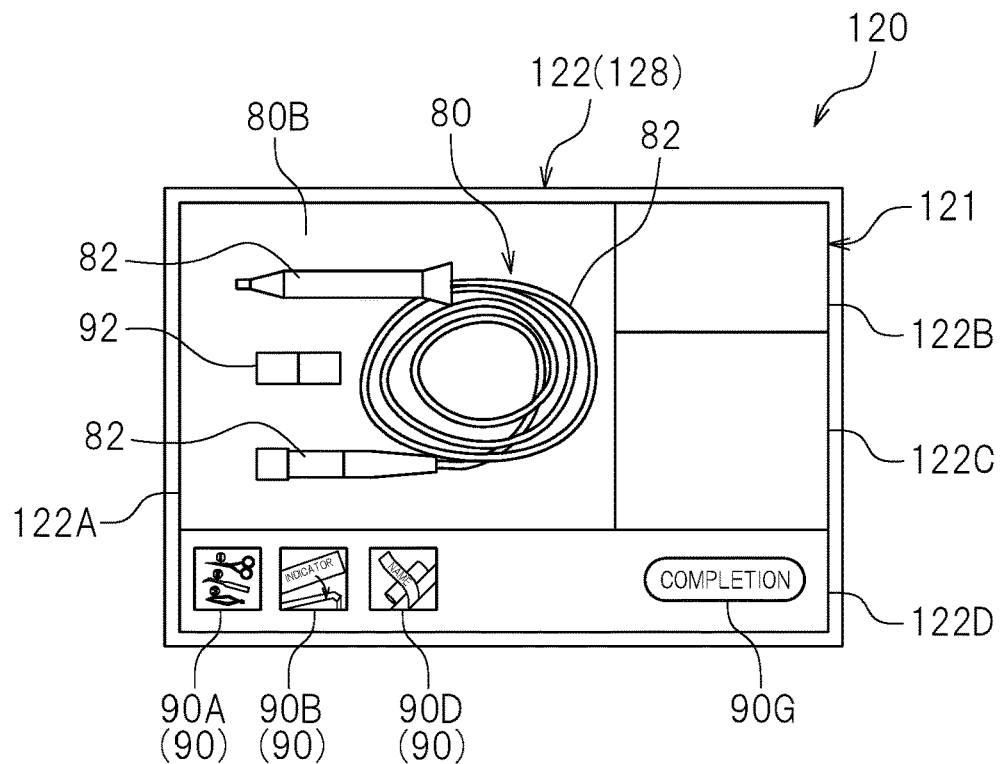
FIG. 26 is a view illustrating a state where an information display screen is displayed on a display screen according to a preferred embodiment of the present invention.
Figure 27:
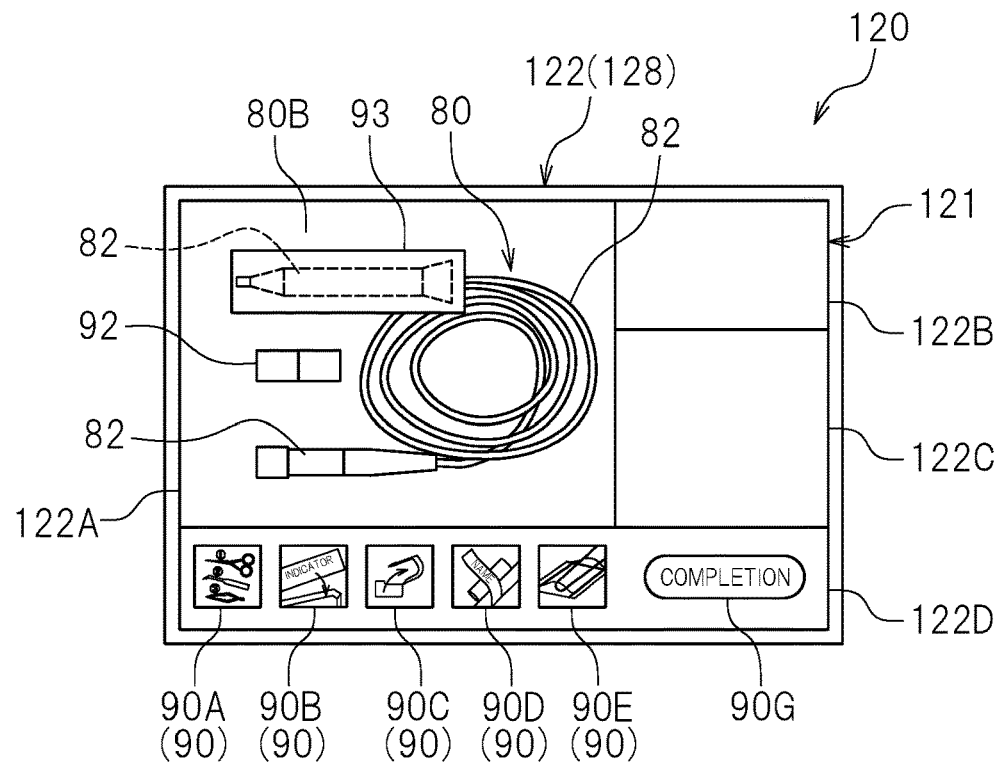
FIG. 27 is a view illustrating a state where an information display screen is displayed on a display screen according to a preferred embodiment of the present invention.

Although the information on the surgical instrument set 80 in the preferred embodiment described above is associated with the number check icon 90A, the indicator check icon 90B, the name input icon 90C, and the sealing member attachment icon 90D, but the number and types of the icons 90 are not limited to these examples. For example, as illustrated in FIG. 26, the icon editor 56 is able to delete association with the name input icon 90C from the information on the surgical instrument set 80. Alternatively, as illustrated in FIG. 27, the icon editor 56 is able to establish a new association between the information on the surgical instrument set 80 and a packing check icon 90E. Here, the packing check icon 90E represents details of a work of determining that surgical instruments 82 are packaged in a bag 93.

Although the surgical instrument set management system 110 includes the server 40 and the portable terminals 120 in the preferred embodiment described above, the present invention is not limited to this example. For example, as long as each of the portable terminals 120 includes the memory 42 and other sections included in the server 40, the portable terminals 120 alone is able to manage the surgical instrument set 80.

In the circulation cycle described above, in some steps, checking of a single surgical instrument and checking of a surgical instrument set are performed after details of works are checked before works in the steps are performed. However, these check works are performed at the same time, check works are complex and complicated.

In view of this, another preferred embodiment of the present invention provides a surgical instrument set management system that reduces a workload on an operator by easing checking of details of works and can enhance quality of a check work.

Inventors of the present invention had an idea of representing details of works in checking by icons and establishing association between the icons and surgical instrument sets so as to alleviate a workload in check works. The inventors also had an idea of enhancing quality of a check work by forcibly making an operator who performs a current step different from an operator who performed the immediately preceding step.

A preferred embodiment of the present invention provides a surgical instrument set management system. The surgical instrument set management system is a surgical instrument set management system that manages a surgical instrument set that includes a plurality of surgical instruments and is previously associated with icons indicating details of works to be checked in a surgery cycle constituted by a surgery step, a collection step, a cleaning step, an assembly step, a sterilization step, and a storage step. The surgical instrument set management system includes: a memory that stores information on the surgical instrument set and icons associated with the information on the surgical instrument set; a display screen that displays the information on the surgical instrument set and the icons associated with the information on the surgical instrument set; a first display that causes the display screen to display the information on the surgical instrument set and the icons associated with the information on the surgical instrument set; an input device to which a confirmation of details of works indicated by the icon is input by an operator; a second display that causes the display screen to display details input with the input device; an operator information acquirer that acquires information on an operator; and a first determiner that determines whether an operator who performs a current step is identical to an operator who performed the immediately preceding step or not. If the first determiner determines that the operators are identical, the first display does not cause the display screen to display the information on the surgical instrument set and the icons associated with the information on the surgical instrument set.

In this configuration, since details of works in the steps of the circulation cycle are represented by icons that are displayed on the display screen, even a beginner operator is able to easily understand the details of works. In addition, since details of works represented by icons are associated with the surgical instrument sets beforehand, it is possible to prevent details of works in the steps from varying among operators. Furthermore, since check results of details of works are displayed on the display screen, missing of checking for details of works is reduced or prevented, and progress statuses of other operators is able to be checked. In a case where the first determiner determines that an operator performing a current step is identical to an operator who performed the immediately preceding step, the first display does not cause the display screen to display information on the surgical instrument set and the icons associated with the information on the surgical instrument set. Accordingly, it becomes necessary to make an operator performing a current step different from an operator who performed the immediately preceding step, and thus, double checking by different operators is able to be performed. As a result, quality of the check work is able to be enhanced.

In a preferred embodiment of the present invention, the surgical instrument set management system further includes a second determiner that determines whether a confirmation of all the icons associated with the information on the surgical instrument set is input with the input device or not. If the second determiner determines that the confirmation of all the icons has been input, the input device may accept an input of completion of all the details of works by an operator.

In this preferred embodiment, unless a confirmation of at least one of the icons associated with the information on the surgical instrument set is input, an operator cannot input completion of all the works through the input device. Accordingly, a failure in checking details of a work is able to be prevented.

In another preferred embodiment of the present invention, each of the surgical instruments of the surgical instrument set includes an identification unit associated with information on the surgical instrument set, the surgical instrument set management system further includes an information acquisition device that acquires information on the identification unit, and when the information on the identification unit is acquired by the information acquisition device, the first display causes the display screen to display the information on the surgical instrument set and the icon associated with the information on the surgical instrument set.

In this preferred embodiment, icons associated with the surgical instrument set are displayed on the display screen only by acquiring information on the identification unit of one of the surgical instruments of the surgical instrument set. Thus, working efficiency is enhanced.

In another preferred embodiment of the present invention, the surgical instrument set management system further includes an icon editor that edits the icon associated with the information on the surgical instrument set.

In this preferred embodiment, even in a case where details of works in the steps for the surgical instrument set change, failures in checking details of works after the change and checking details of works are prevented by editing icons (e.g., addition of an icon or deletion of an icon).

In another preferred embodiment of the present invention, the input device is a touch panel disposed on the display screen.

In this preferred embodiment, an operator is able to easily input a confirmation of details of a work by directly touching the display screen.

In another preferred embodiment of the present invention, the icons include a number check icon indicating a work of checking the number of surgical instruments included in the surgical instrument set.

In another preferred embodiment of the present invention, the icons include an indicator check icon indicating a work of checking sealing of an indicator in the surgical instrument set.

In another preferred embodiment of the present invention, the icon includes a check icon indicating a work of checking packing of the surgical instruments.

In another preferred embodiment of the present invention, the icons include a name input icon indicating a work of housing the surgical instrument set in a predetermined case, attaching a sterilization tape to an opening/closing portion of the case, and writing the name of an operator on the sterilization tape.

In another preferred embodiment of the present invention, the icons include a sealing member attachment icon indicating a work of attaching a sealing member for inhibiting opening and closing of the case to the case.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A medical tool work support system that supports a work on a medical tool in a work step using the medical tool, the work step being a step to be performed for surgery using the medical tool, the step to be performed for surgery including at least one of collecting the medical tool after the surgery, cleaning the medical tool after the surgery, assembling the medical tool after the cleaning, sterilizing the medical tool after the assembly, and storing the medical tool after the sterilizing, the medical tool work support system comprising:
   a display;
   a memory that stores data indicating a work procedure on the medical tool in the work step; and
   a display controller that causes the display to display the work procedure based on the data stored in the memory, wherein the memory stores video data regarding the work procedure;

the display controller is configured or programmed to cause the display to display a video based on the video data;

the medical tool includes at least a first member and a second member positioned relative to the first member;

the second member relative to the first member; and the display controller is configured to cause the display to display the positioning procedure based on the video data.

2. The medical tool work support system according to claim 1, wherein the video data includes an illustration.

3. The medical tool work support system according to claim 1, wherein the memory stores still image data of an illustration indicating the work procedure; and the display controller is configured or programmed to cause the display to display a still image based on the still image data.

4. The medical tool work support system according to claim 3, wherein the still image includes a cross-sectional view of the medical tool.

5. The medical tool work support system according to claim 3, wherein the still image includes an enlarged view of the medical tool.

6. A medical tool work support system that supports a work on a medical tool in a work step using the medical tool, the work step being a step to be performed for surgery using the medical tool, the step to be performed for surgery including at least one of collecting the medical tool after the surgery, cleaning the medical tool after the surgery, assembling the medical tool after the cleaning, sterilizing the medical tool after the assembly and storing the medical tool after the sterilizing, the medical tool work support system comprising:

a display;

a memory that stores data indicating a work procedure on the medical tool in the work step; and a display controller that causes the display to display the work procedure based on the data stored in the memory, wherein the memory stores video data regarding the work procedure;

the display controller is configured or programmed to cause the display to display a video based on the video data;

the medical tool includes a manipulator and an operator that operates in conjunction with an operation by the manipulator;

the work procedure is a work procedure of operating the operator by the manipulator; and the display controller is configured or programmed to cause the display to display the work procedure based on the video data.

7. A medical tool work support system that supports a work on a medical tool in a work step using the medical tool, the work step being a step to be performed for surgery using the medical tool, the step to be performed for surgery including at least one of collecting the medical tool after the surgery, cleaning the medical tool after the surgery, assembling the medical tool after the cleaning, sterilizing the medical tool after the assembly, and storing the medical tool after the sterilizing, the medical tool work support system comprising:

a display;

a memory that stores data indicating a work procedure on the medical tool in the work step; and a display controller that causes the display to display the work procedure based on the data stored in the memory, wherein the data includes main work data indicating details of one or more main works included in the work step and detailed work data indicating details of one or more detailed works of each of the main works;

the medical tool work support system further comprising a selector that selects whether the details of the detailed work data are displayed or not; and the display controller causes the display to display the details of the main work data and to display the details of the detailed work data depending on selection by the selector.

8. The medical tool work support system according to claim 7, wherein a display based on the main work data includes a portion represented in a first color and a display based on the detailed work data includes a portion represented in a second color different from the first color.

9. The medical tool work support system according to claim 8, wherein one of the main works is set as a quality priority work; and a display based on main work data of the main work set as the quality priority work includes a portion represented in a third color different from the first color and the second color.

10. The medical tool work support system according to claim 9, wherein a display based on the main work data of the main work set as the quality priority work includes a checker that is pressed when the main work is completed;

the medical tool work support system further comprises a detector that detects whether the checker is pressed or not; and the display controller is configured or programmed such that when the detector does not detect that the checker is pressed, the display controller does not cause the display to display a detail of the main work data of another main work next to the main work set as the quality priority work or does not cause the display to provide a completion display.

11. The medical tool work support system according to claim 7, wherein the detailed work data includes video data.

12. The medical tool work support system according to claim 11, wherein the video data is data indicating a positioning procedure of, in assembling a plurality of parts of the medical tool, positioning one of the plurality of parts relative to another of the plurality of parts.

13. The medical tool work support system according to claim 7, wherein the detailed work data includes illustration data indicating a cross-sectional view or an enlarged view of the medical tool.

14. The medical tool work support system according to claim 7, wherein the detailed work data includes photograph data.

* * * * *